United States Patent [19]
Pittet et al.

[11] Patent Number: 4,515,968
[45] Date of Patent: May 7, 1985

[54] FURYL AND PHENYL MERCAPTALS AND USE THEREOF IN AUGMENTING OR ENHANCING THE AROMA OR TASTE OF FOODSTUFFS

[75] Inventors: Alan O. Pittet, Atlantic Highlands; Thomas F. Courtney, Jr., Oakhurst; Ranya Muralidhara, Fair Haven, all of N.J.

[73] Assignee: International Flavors & Fragrances Inc., New York, N.Y.

[21] Appl. No.: 541,151

[22] Filed: Oct. 12, 1983

[51] Int. Cl.$^3$ .................. C02D 333/00; A23C 3/00
[52] U.S. Cl. .................. 549/39; 549/502; 426/536
[58] Field of Search .............. 549/30, 502, 39; 568/57, 66; 426/536

[56] References Cited

U.S. PATENT DOCUMENTS

| | | | |
|---|---|---|---|
| 2,864,739 | 12/1958 | Scott et al. | 568/57 |
| 3,075,020 | 1/1963 | Webb | 568/57 |
| 3,653,920 | 4/1972 | Brinkman | 568/57 |
| 3,931,245 | 1/1976 | Winter et al. | 549/502 |
| 3,952,024 | 4/1976 | Winter et al. | 549/502 |
| 4,220,561 | 9/1980 | Winter | 549/30 |
| 4,374,998 | 2/1983 | Boden | 549/30 |

FOREIGN PATENT DOCUMENTS 50-64211  5/1975  Japan .................. 568/57

*Primary Examiner*—Alan Siegel
*Attorney, Agent, or Firm*—Arthur L. Liberman

[57] ABSTRACT

Described are furyl and phenyl mercaptals defined according to the generic structure:

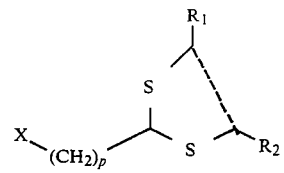

wherein the dashed line represents a carbon-carbon single bond or no bond; wherein $R_1$ and $R_2$ are the same or different and each represents hydrogen, methyl or ethyl; wherein p is 0 or 1; and wherein X represents a phenyl moiety having the structure:

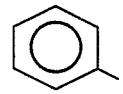

or a furyl moiety having the structure:

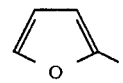

and uses thereof in augmenting or enhancing the aroma or taste of foodstuffs.

3 Claims, 20 Drawing Figures

FIG.1
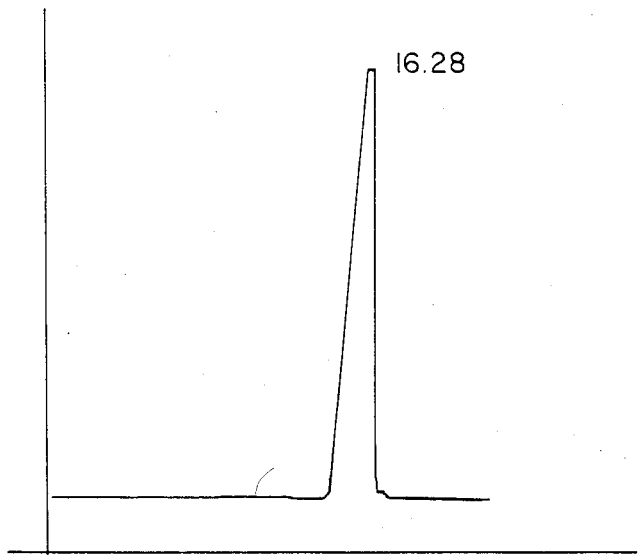
GLC PROFILE FOR FRACTION 3 OF EXAMPLE I.
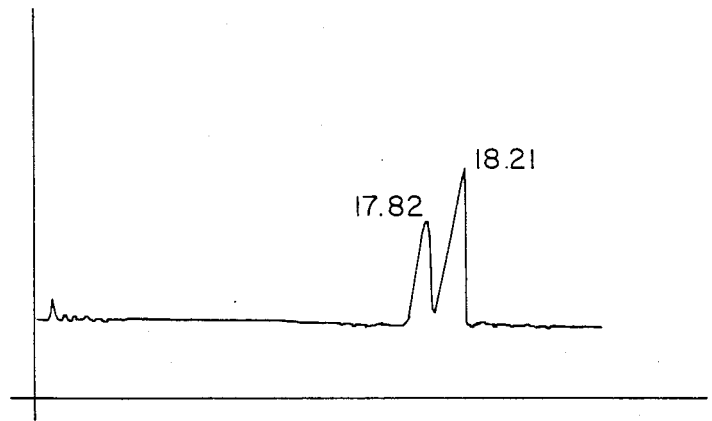
GLC PROFILE FOR EXAMPLE II CRUDE
FIG.3

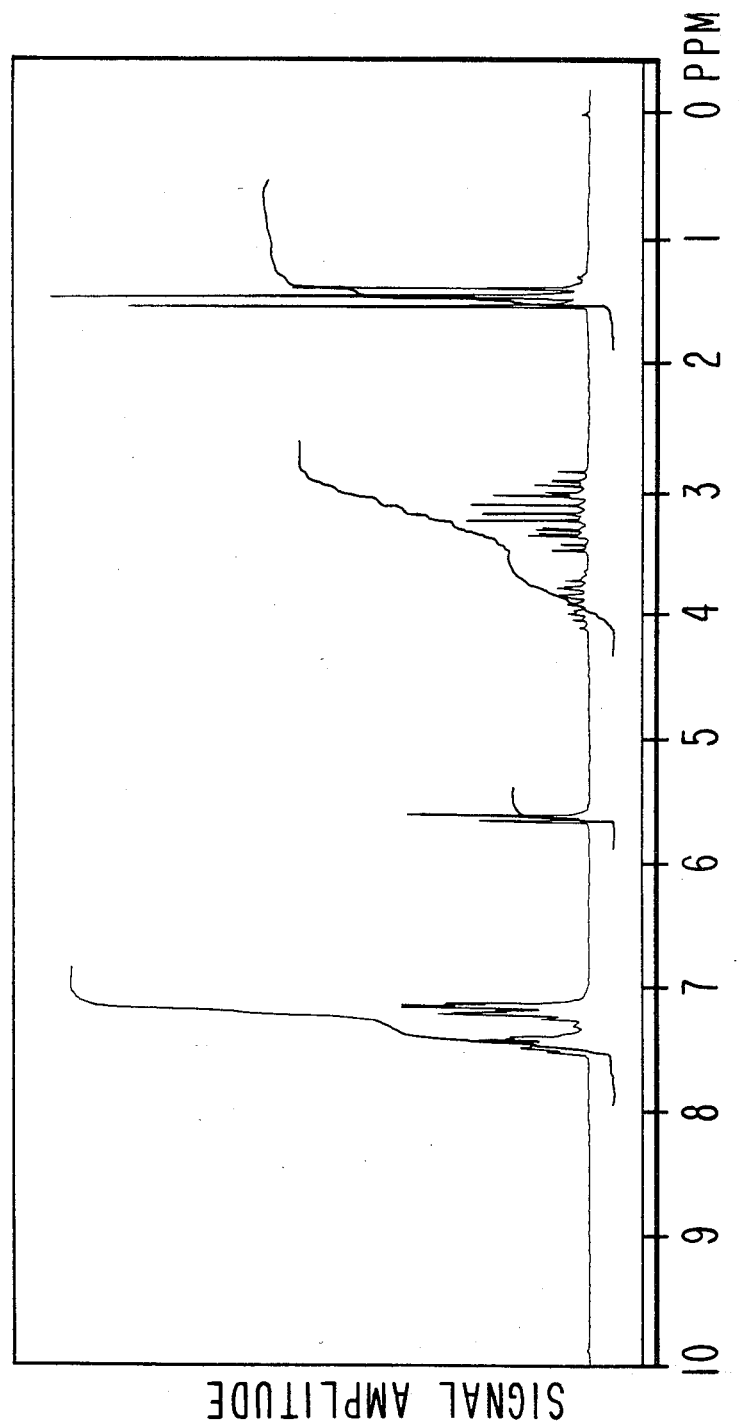

FIG. 4
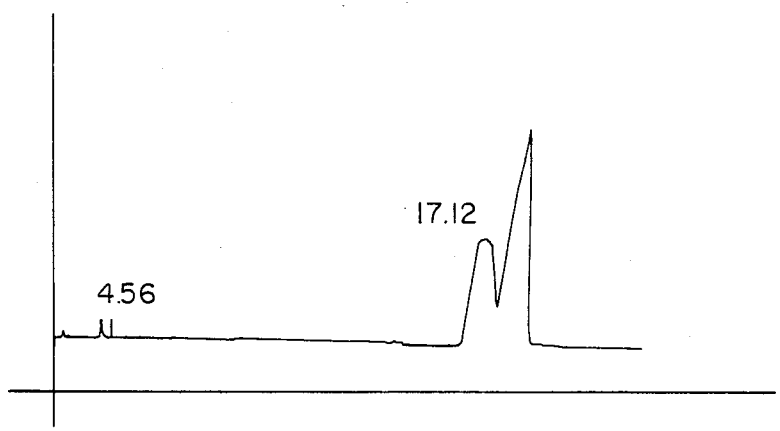
GLC PROFILE FOR FRACTION 4 OF EXAMPLE II.
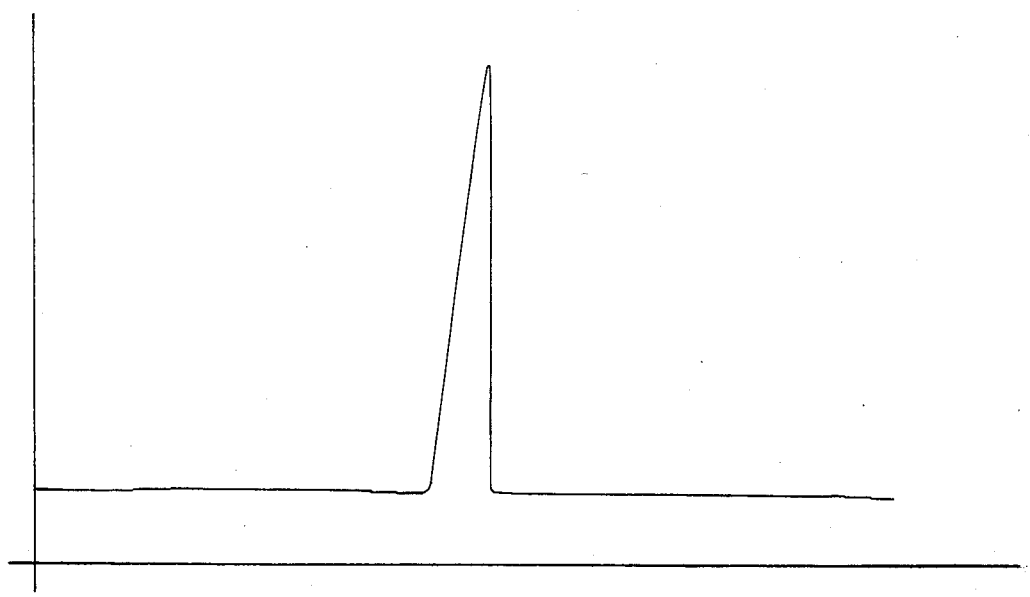
GLC PROFILE FOR FRACTION 4 OF EXAMPLE III.
FIG. 6

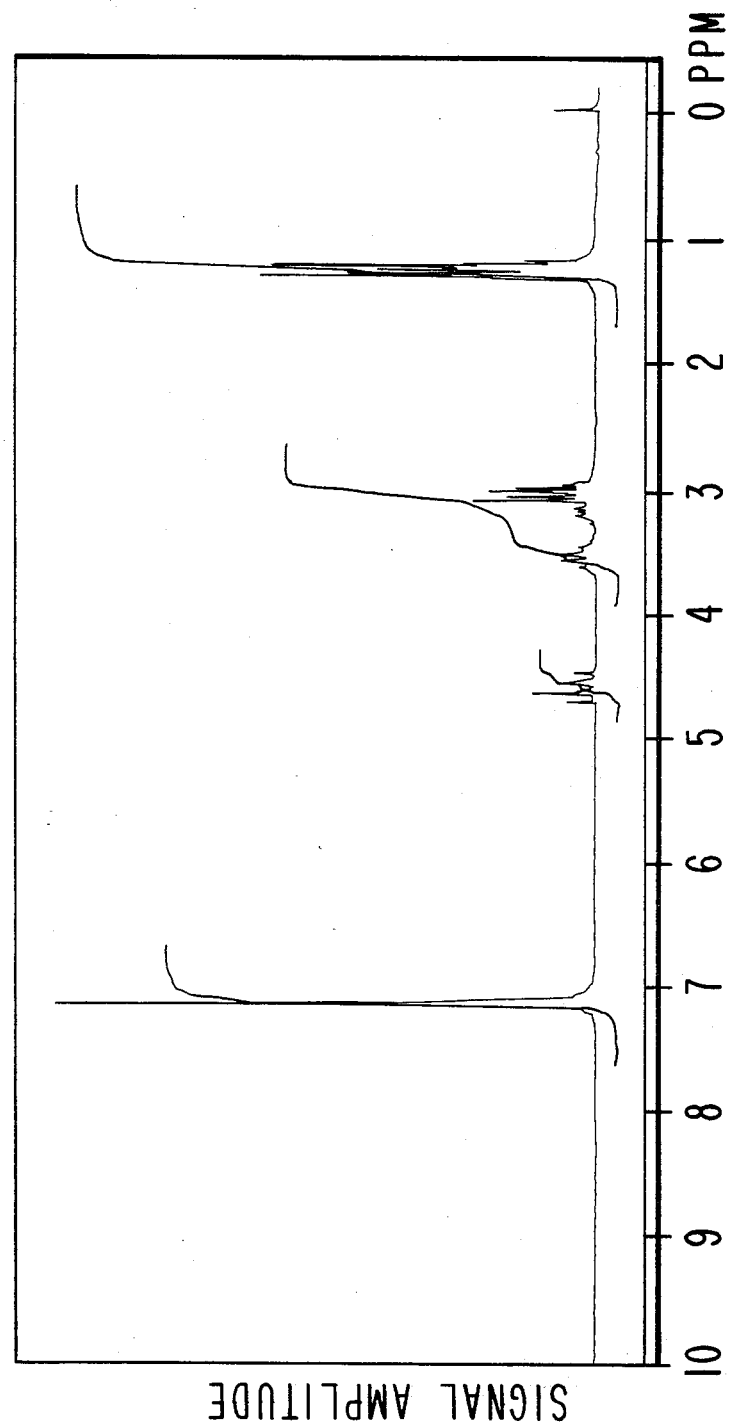

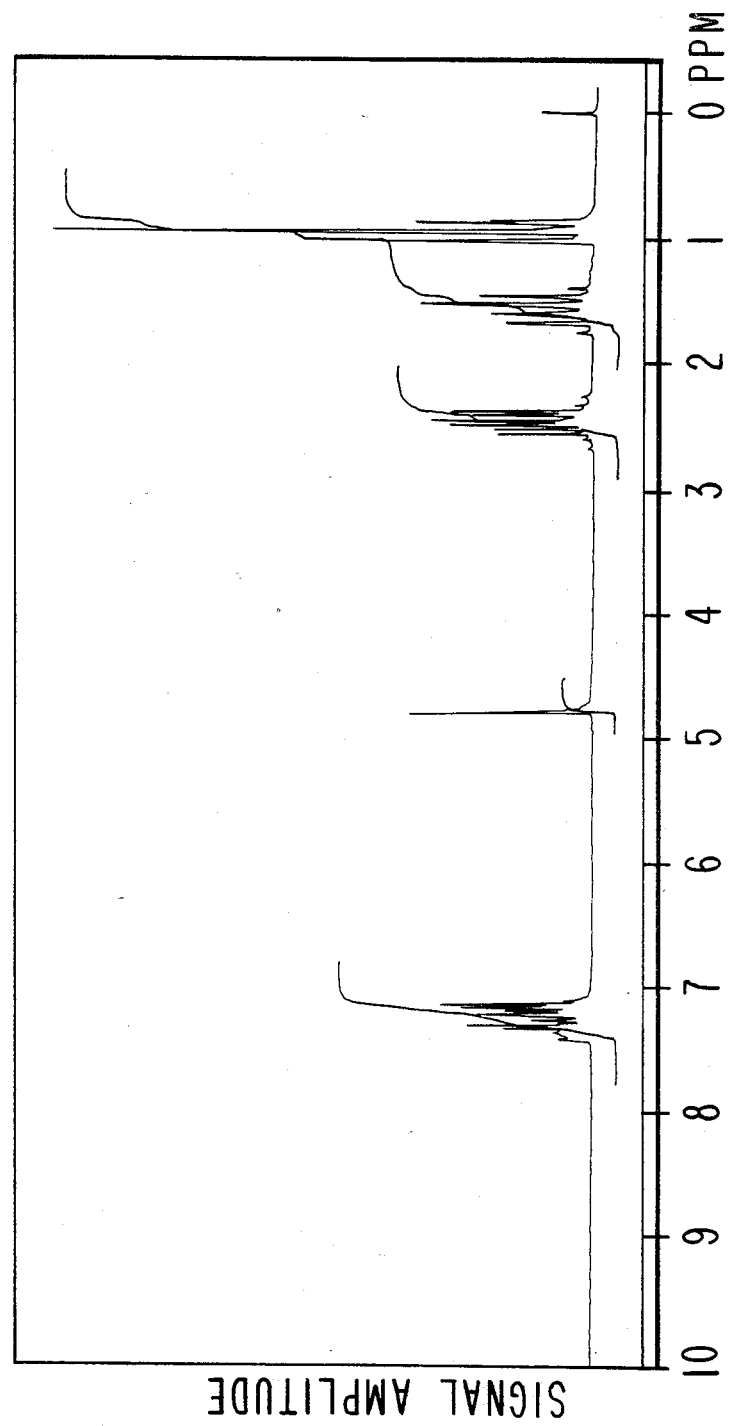

FIG.8
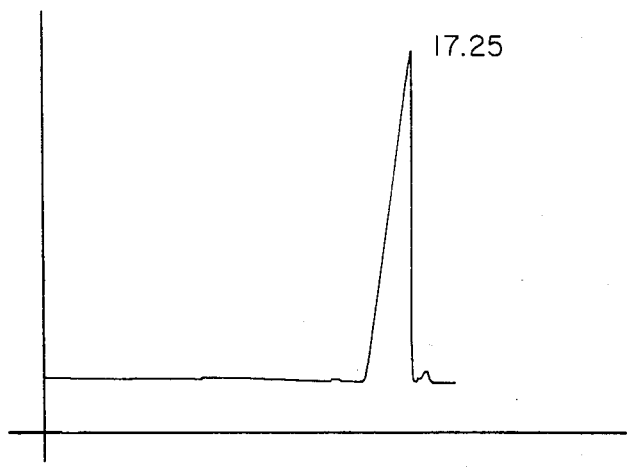
GLC PROFILE FOR FRACTION 3
OF EXAMPLE IV.
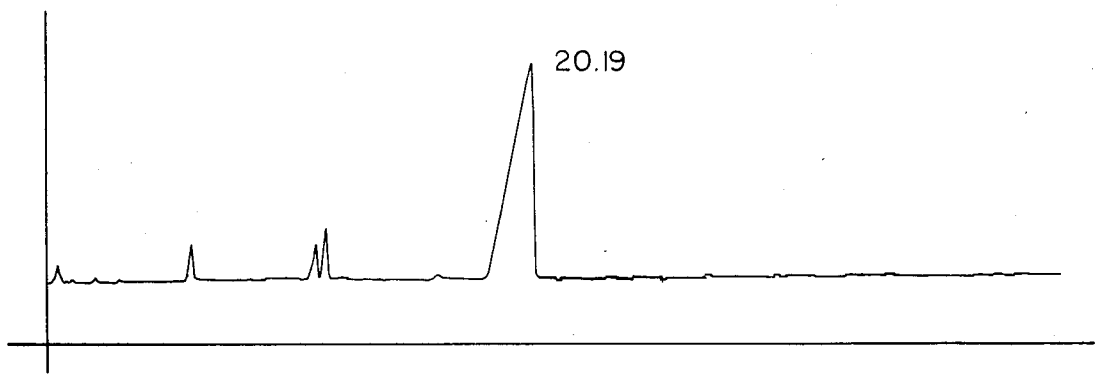
GLC PROFILE FOR EXAMPLE V, "CRUDE".
FIG.10

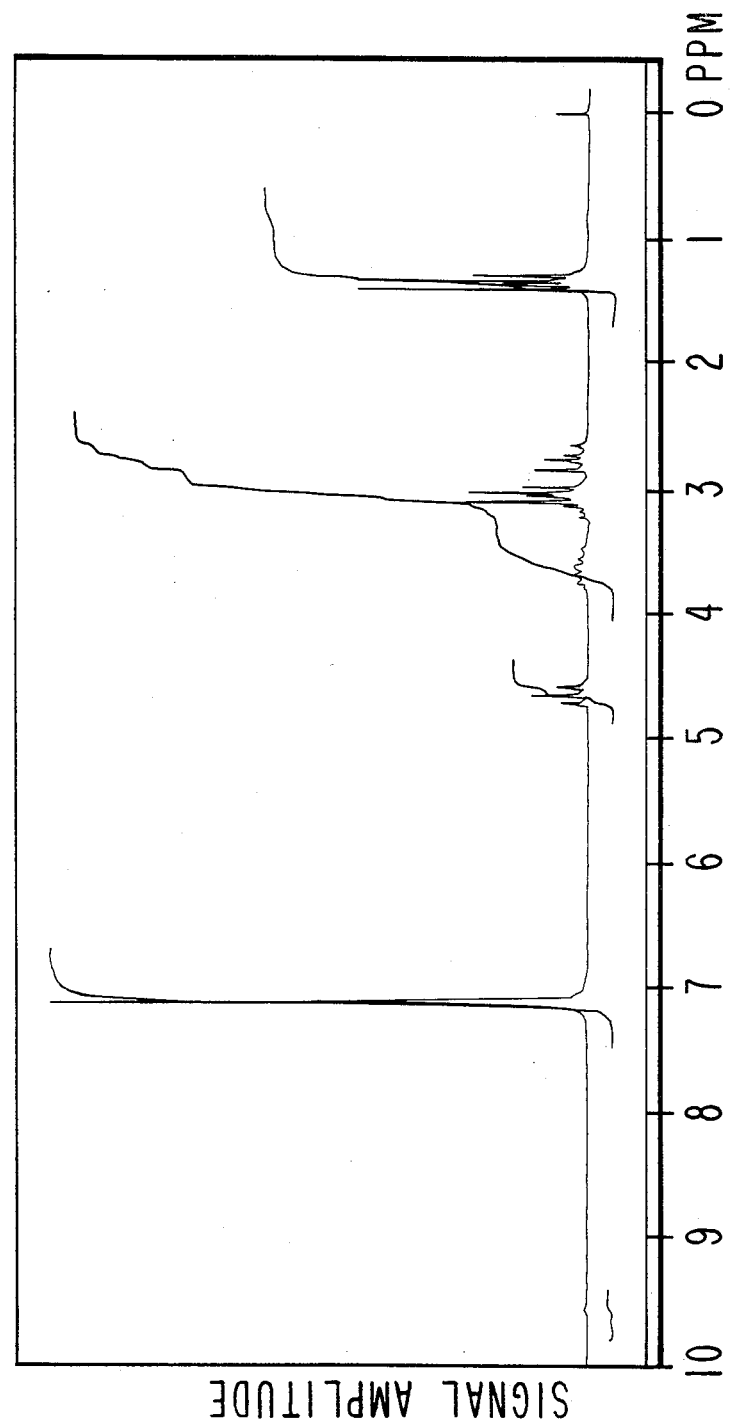

FIG.11
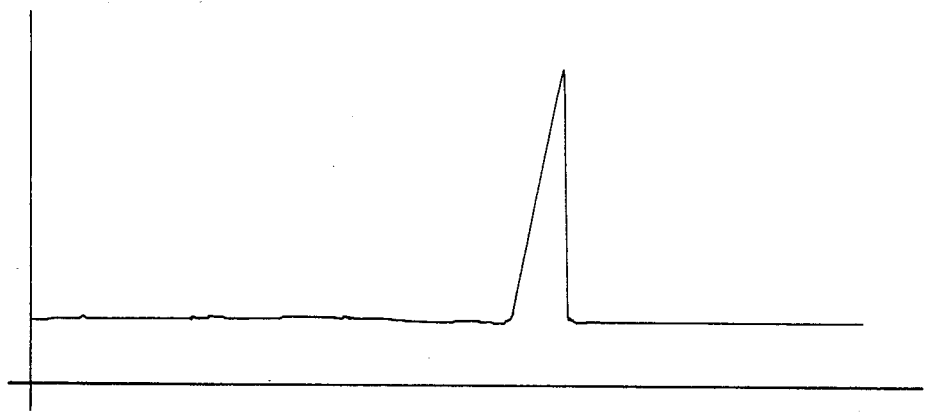
GLC PROFILE FOR FRACTION 4 OF EXAMPLE V.
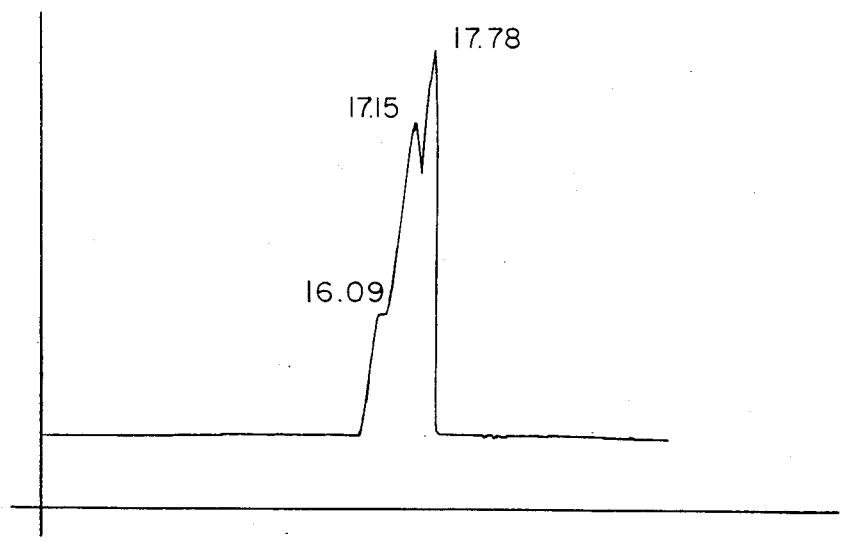
GLC PROFILE FOR FRACTION 2 OF EXAMPLE VI.
FIG.13

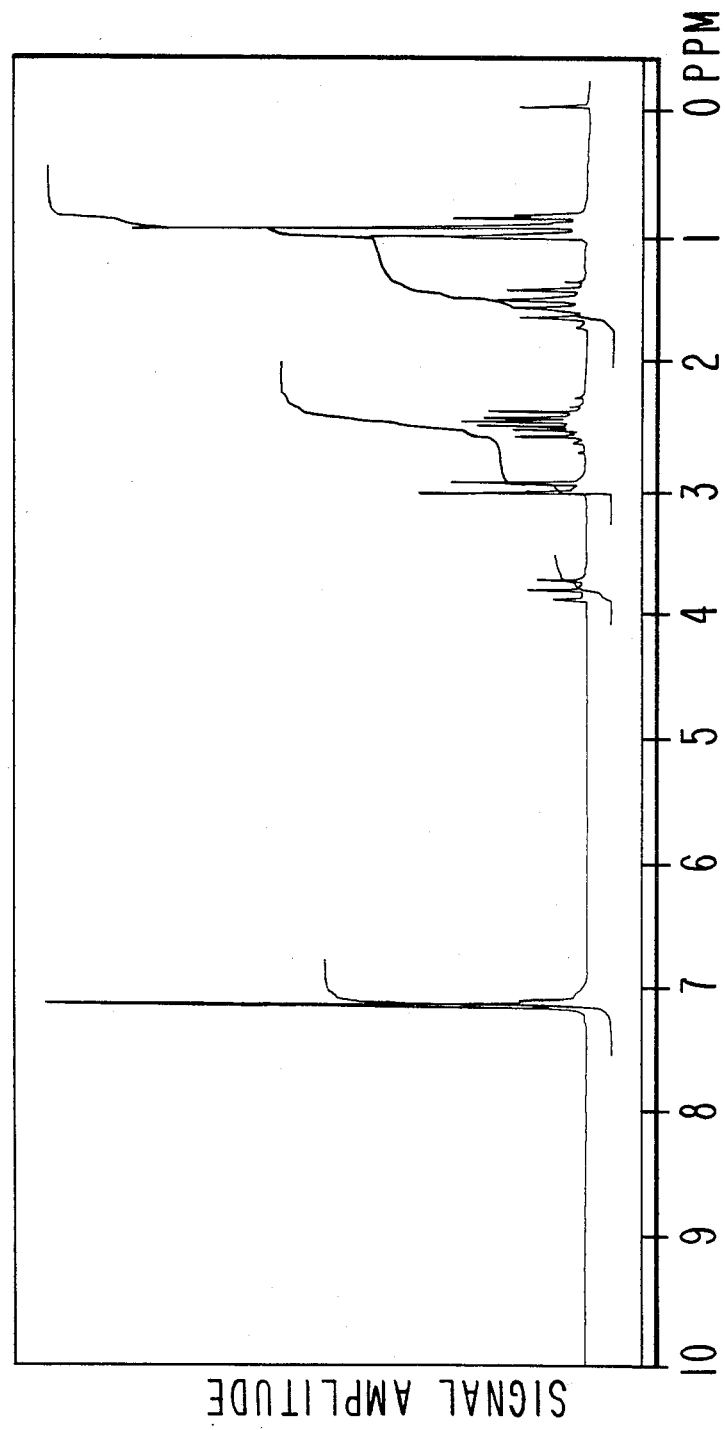
FIG.12 NMR SPECTRUM FOR FRACTION 4 OF EXAMPLE V.

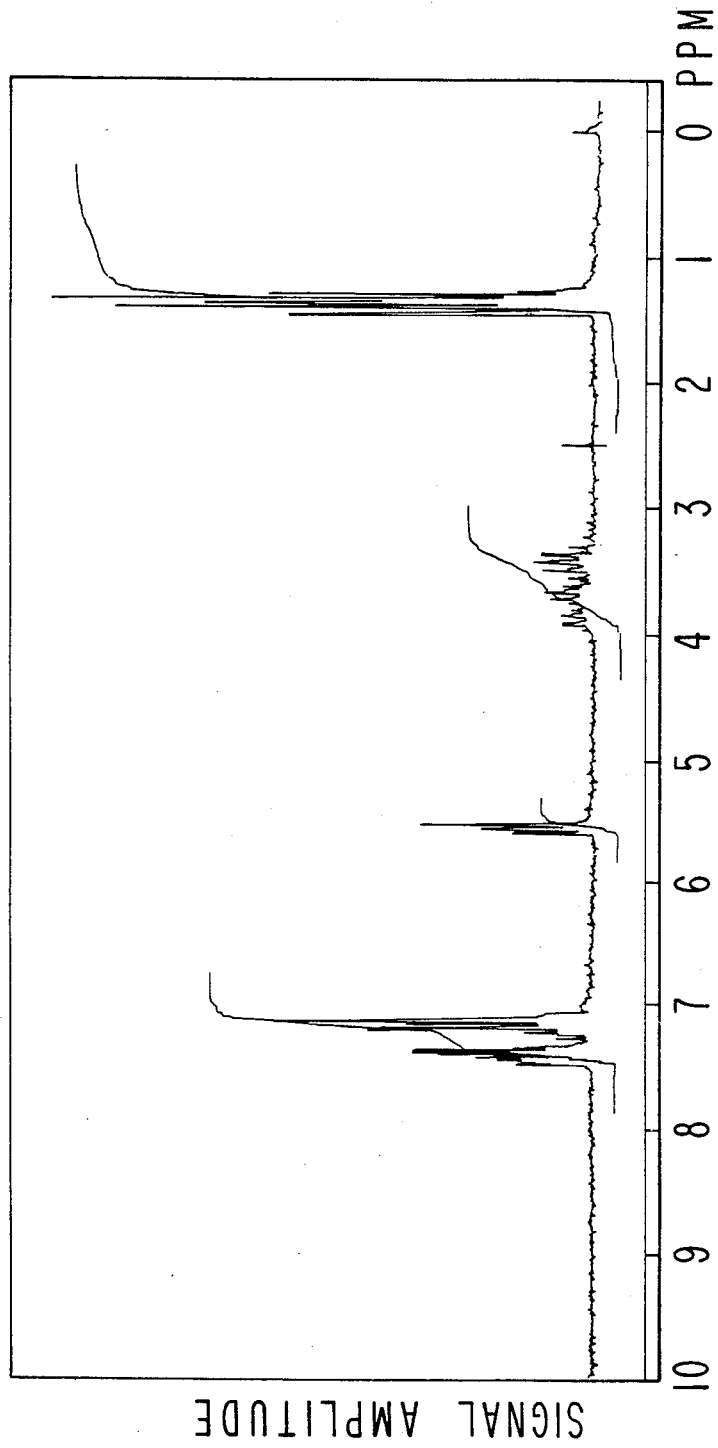
FIG. 14 NMR SPECTRUM FOR FRACTION 2 OF EXAMPLE VI

FIG.15
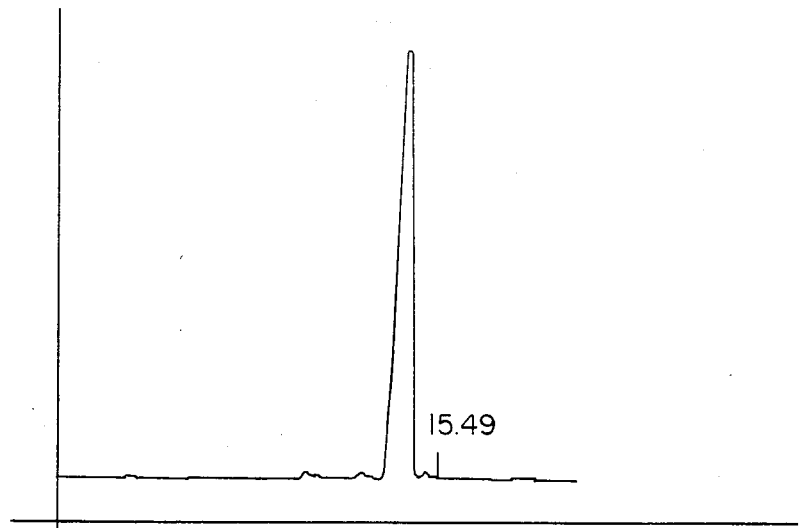
GLC PROFILE FOR FRACTION 2
OF EXAMPLE VII
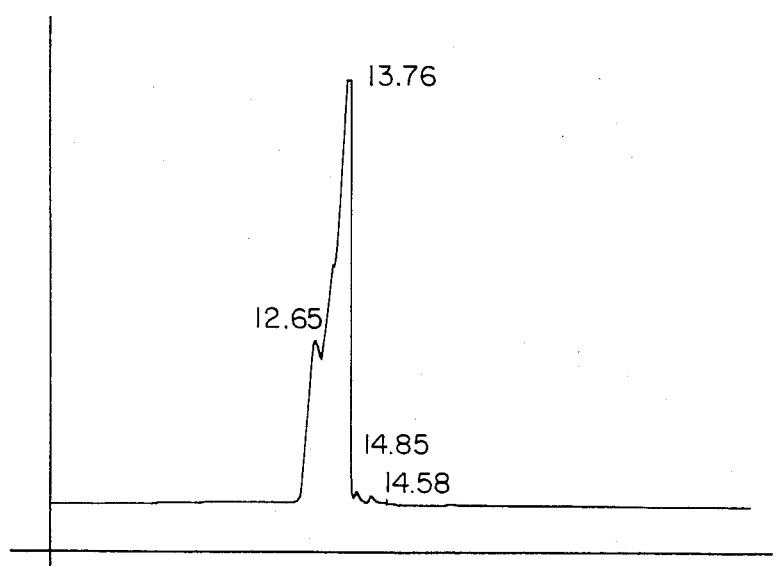
GLC PROFILE FOR FRACTION 3
OF EXAMPLE VIII.
FIG.17

NMR SPECTRUM FOR FRACTION 2 OF EXAMPLE VII

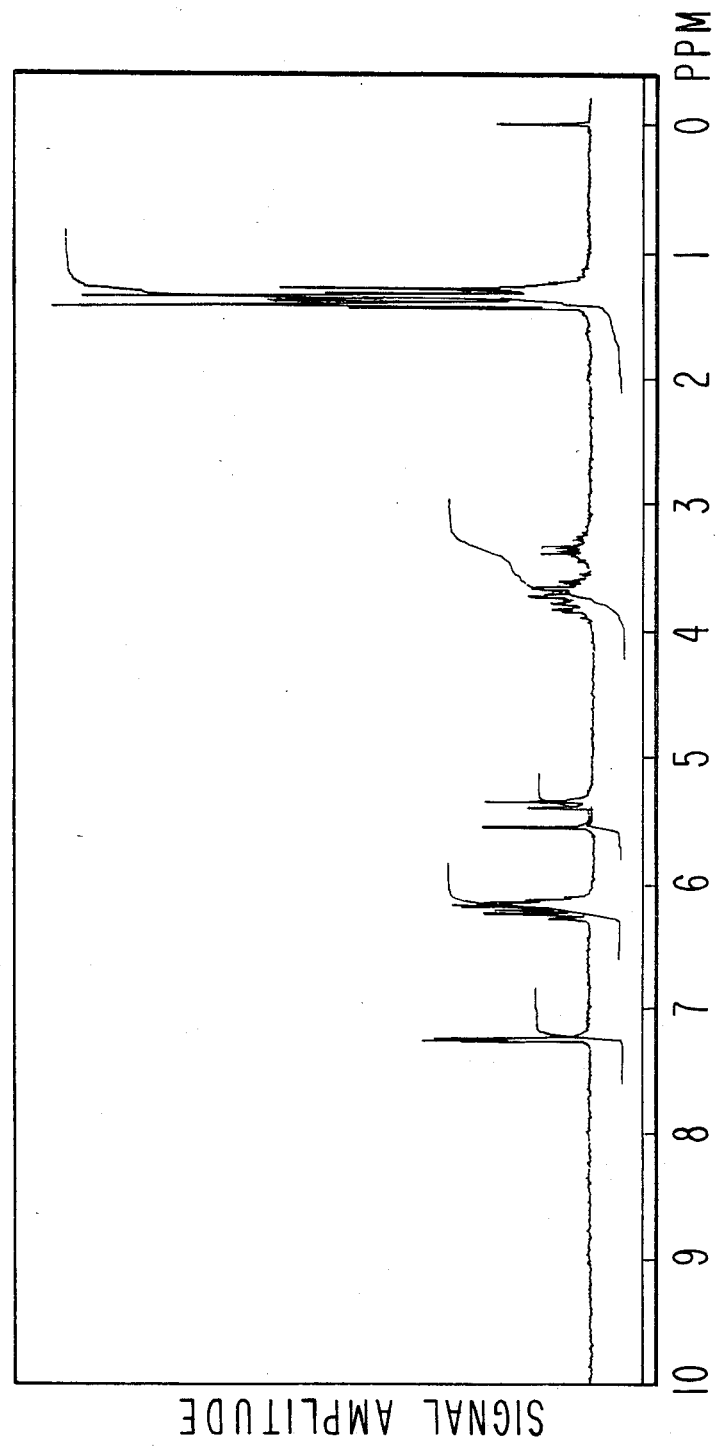

GLC PROFILE FOR FRACTION 2 OF EXAMPLE IX.

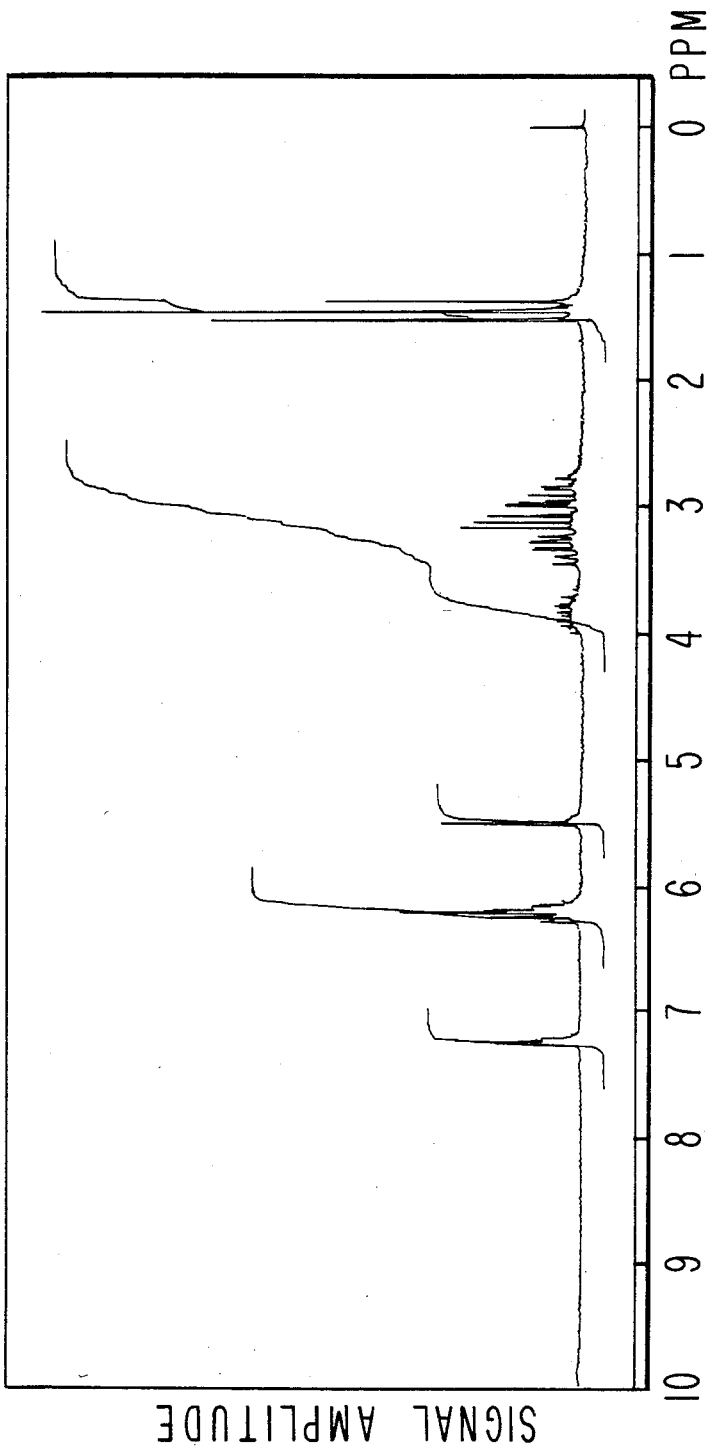

FURYL AND PHENYL MERCAPTALS AND USE THEREOF IN AUGMENTING OR ENHANCING THE AROMA OR TASTE OF FOODSTUFFS

BACKGROUND OF THE INVENTION

This invention relates to furyl and phenyl mercaptals defined according to the generic structure:

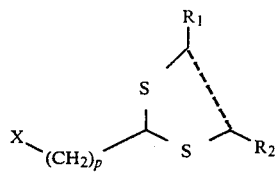

wherein the dashed line represents a carbon-carbon single bond or no bond; wherein $R_1$ and $R_2$ are the same or different and each represents hydrogen, methyl or ethyl; wherein p is 0 or 1; and wherein X represents a phenyl moiety having the structure:

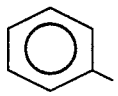

or a furyl moiety having the structure:

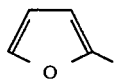

and uses thereof in augmenting or enhancing the aroma or taste of foodstuffs, particularly roasted nut, roasted meat, beef broth, black pepper, onion, fine herbs omelet and cooked onion omelet flavored foodstuffs.

There has been considerable work performed relating to substances which can be used to impart (modify, augment or enhance) flavors to (or in) foodstuffs. These substances are used to diminish the use of natural materials some of which may be in short supply and to provide more uniform properties in the finished product.

Roasted, green vegetable, brothy, savory, pepper, eggy, green, herbaceous, floral, fine herbs omelet-like, black pepper-like, onion-like, tobacco-like, and cooked onion omelet-like aroma and taste nuances with hydrolyzed vegetable protein-like aftertastes and lachrymatory (raw fresh onion-like) effects are particularly desirable for uses in many foodstuff flavors particularly in roasted nut, roasted meat, beef broth, black pepper, onion, cooked onion omelet and fine herbs omelet flavored foodstuffs (for example, omelets made using powdered egg) and also in proteinaceous food substances which have little or no flavor value such as dried fish meal and a number of soy protein products as well as miso bean paste as described in Japanese published application number J78/001840 of Jan. 28, 1978.

Mercaptals of carbonyl derivatives are known in the prior art for augmenting or enhancing the aroma or taste of foodstuffs. Thus, mercaptals covered by the genus having the structure:

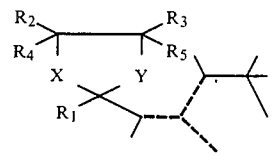

wherein $R_1$ represents $C_1$–$C_3$ lower alkyl; $R_2$, $R_3$, $R_4$ and $R_5$ represent the same or different hydrogen or $C_1$–$C_3$ lower alkyl; X and Y represent the same or different oxygen or sulfur; and one of the dashed lines represents a carbon-carbon double bond and the other of the dashed lines represent carbon-carbon single bonds are disclosed in U.S. Pat. No. 4,379,754 issued on Apr. 12, 1983 for use in augmenting or enhancing the aroma or taste of foodstuffs.

Many compounds in the prior art are disclosed for augmenting or enhancing onion flavors including providing lachrymatory effects (the effect obtained when eating a raw fresh green onion). Thus, U.S. Pat. No. 3,751,269 issued on Apr. 7, 1973 discloses onion flavoring compounds which provide such lachrymatory effects including thioalkanal-S-oxides and alkyl alkene thiosulfonates.

Black pepper flavor and aroma are provided in application for U.S. patent Ser. No. 774,056 filed on Mar. 3, 1977 (now abandoned).

Arctander, "Perfume and Flavor Chemicals (Aroma Chemicals)" Volume I at Monograph 272 discloses the organoleptic utilities of benzaldehyde ethyleneglycolacetal having the structure:

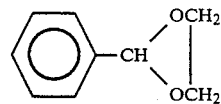

and at Monograph 274 discloses the organoleptic properties of benzaldehyde propyleneglycol acetal having the structure:

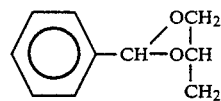

Arctander states that benzaldehyde propyleneglycol acetal is used in flavor compositions for imitation cherry, almond, nut, particularly where greater stability and lower volatility of the "bitter almond" theme is desirable but that the acetal itself is practically odorless "but will liberate benzaldehyde under influence of moisture (particularly in the presence of acid) and heat". Benzaldehyde propyleneglycol acetal is on the G.R.A.S. list as F.E.M.A. number 2130. Arctander further states that benzaldehyde ethyleneglycolacetal is suggested for use in flavor compositions where storage conditions favor a more stable form of benzaldehyde.

Nothing in the prior art discloses the furyl and phenyl mercaptals of our invention or their organoleptic uses.

BRIEF DESCRIPTION OF THE DRAWINGS

FIG. 1 is the GLC profile for fraction 3 of the distillation product of the reaction product of Example I containing the compound having the structure:

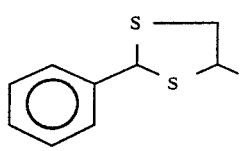

Figure 16:
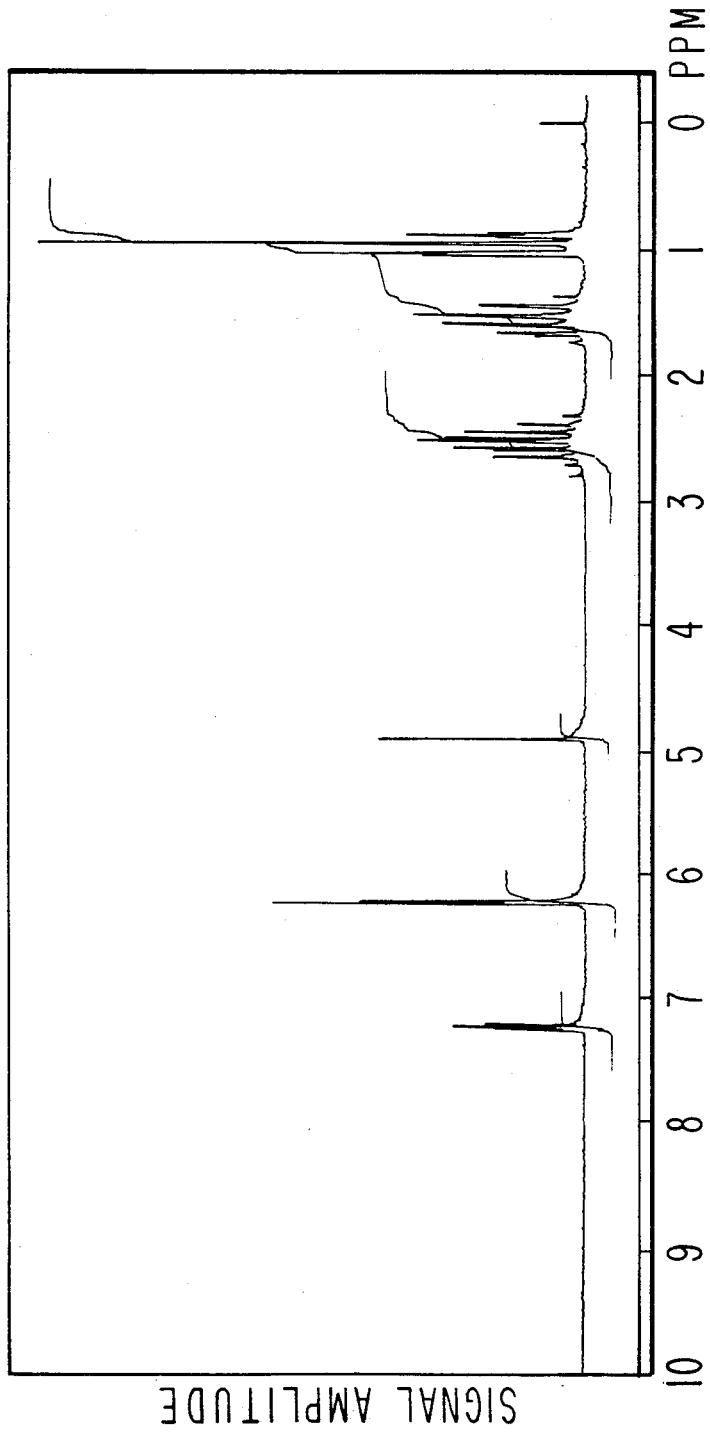

(conditions: SE-30 column, 10'×0.125", programmed at 100°-220° C. at 8° C. per minute).

FIG. 2 is the NMR spectrum for fraction 3 of the distillation product of the reaction product of Example I containing the compound having the structure:

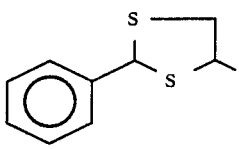

(conditions: Solvent: CFCl₃; Field Strength: 100 MHz).

FIG. 3 is the GLC profile for the crude reaction product of Example II containing the compound having the structure:

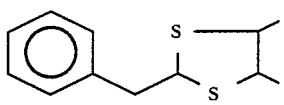

FIG. 4 is the GLC profile for fraction 4 of the distillation product of the reaction product of Example II containing the compound having the structure:

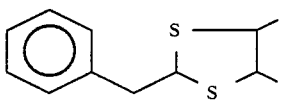

(conditions: 10'×0.125" SE-30 column programmed at 100°-220° C. at 8° C. per minute).

FIG. 5 is the NMR spectrum for fraction 3 of the distillation product of the reaction product of Example II containing the compound having the structure:

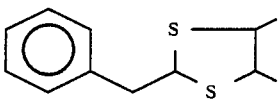

(conditions: Field Strength: 100 MHz; Solvent: CFCl₃).

FIG. 6 is the GLC profile for fraction 4 of the distillation product of the reaction product of Example III containing the compound having the structure:

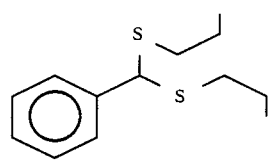

(conditions: 10'×0.125" SE-30 column progrmmed at 100°-220° C. at 8° C. per minute).

FIG. 7 is the NMR spectrum for fraction 4 of the distillation product of the reaction product of Example III containing the compound having the structure:

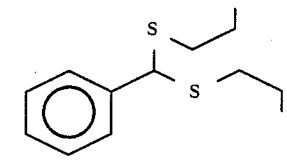

(conditions: Field Strength: 100 MHz; Solvent: CFCl₃).

FIG. 8 is the GLC profile for fraction 3 of the distillation product of the reaction product of Example IV containing the compound having the structure:

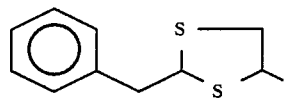

(conditions: 10'×0.125" SE-30 column programmed at 100°-220° C. at 8° C. per minute).

FIG. 9 is the NMR spectrum for fraction 3 of the distillation product of the reaction product of Example IV containing the compound having the structure:

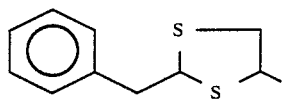

FIG. 10 is the GLC profile for the crude reaction product of Example V containing the compound having the structure:

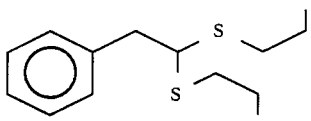

FIG. 11 is the GLC profile for fraction 4 of the distillation product of the reaction product of Example V containing the compound having the structure:

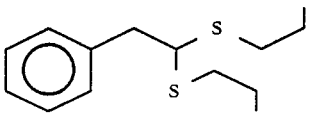

(conditions: 10'×0.125" SE-30 column programmed at 100°-220° C. at 8° C. per minute).

FIG. 12 is the NMR spectrum for fraction 4 of the distillation product of the reaction product of Example V containing the compound having the structure:

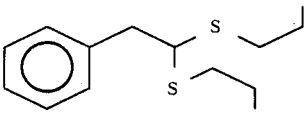

(conditions: Field Strength: 100 MHz; Solvent: CFCl₃).

FIG. 13 is the GLC profile for fraction 2 of the distillation product of the reaction product of Example VI containing the compound having the structure:

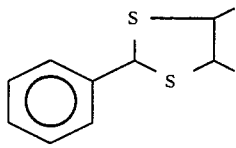

FIG. 14 is the NMR spectrum for fraction 2 of the distillation product of the reaction product of Example VI containing the compound having the structure:

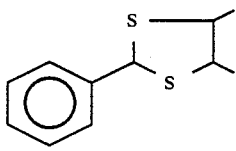

(conditions: Field Strength: 100 MHz; Solvent: CFCl₃).

FIG. 15 is the GLC profile for fraction 2 of the distillation product of the reaction product of Example VII containing the compound having the structure:

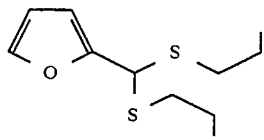

(conditions: 10'×0.125" SE-30 column programmed at 100°-220° C. at 8° C. per minute).

FIG. 16 is the NMR spectrum for fraction 2 of the distillation product of the reaction product of Example VII containing the compound having the structure:

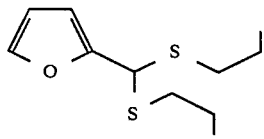

(conditions: Field Strength: 100 MHz; Solvent: CFCl₃).

FIG. 17 is the GLC profile for fraction 3 of the distillation product of the reaction product of Example VIII containing the compound having the structure:

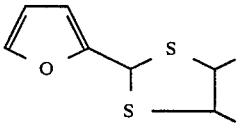

(conditions: 10'×0.125" SE-30 column programmed at 100°-220° C. at 80° C. per minute).

FIG. 18 is the NMR spectrum for fraction 3 of the distillation product of the reaction product of Example VIII containing the compound having the structure:

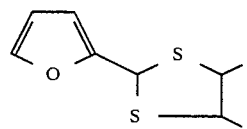

(conditions: Field Strength: 100 MHz; Solvent: CFCl₃).

Figure 19:
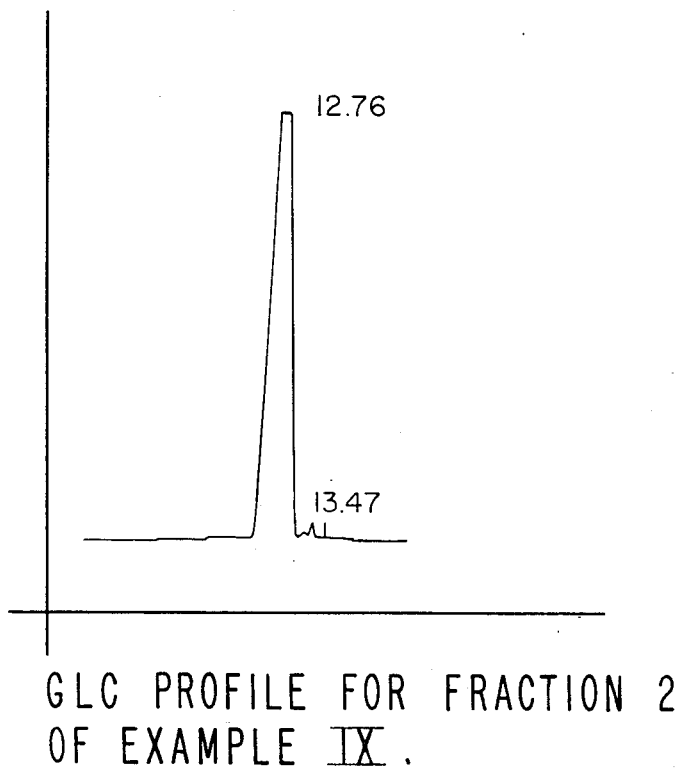

FIG. 19 is the GLC profile for fraction 2 of the distillation product of the reaction product of Example IX containing the compound having the structure:

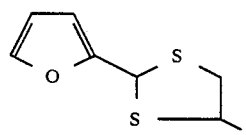

(conditions: 10'×0.125" SE-30 column programmed at 100°-220° C. at 8° C. per minute).

FIG. 20 is the NMR spectrum for fraction 2 of the distillation product of the reaction product of Example IX containing the compound having the structure:

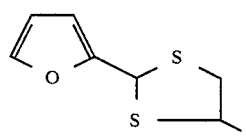

(conditions: Solvent: CFCl₃; Field Strength: 100 MHz).

THE INVENTION

The instant invention provides compounds having the generic structure:

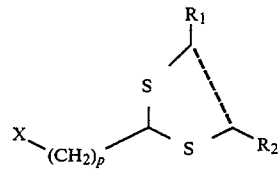

wherein the dashed line represents a carbon-carbon single bond or no bond; wherein $R_1$ and $R_2$ are the same or different and each represents hydrogen, methyl or ethyl; wherein p is 0 or 1; and wherein X represents a phenyl moiety having the structure:

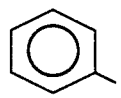

or a furyl moiety having the structure:

The compounds are useful in augmenting or enhancing the aroma and/or taste of foodstuffs.

Briefly, our invention contemplates augmenting or enhancing the aroma or taste of roasted nut, roasted meat, beef broth, black pepper and omelet (onion omelet and fine herbs omelet)-flavored foodstuffs. The compound defined according to the genus:

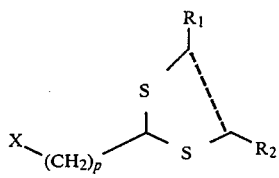

wherein the dashed line represents a carbon-carbon single bond or no bond; wherein $R_1$ and $R_2$ are the same or different and each represents hydrogen, methyl or ethyl; wherein p is 0 or 1; and wherein X represents a phenyl moiety having the structure:

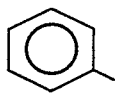

or a furyl moiety having the structure:

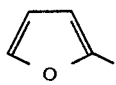

augment or enhance roasted, green vegetable-like, brothy, savory, peppery, eggy, green, herbaceous, floral, fine herbs omelet-like, black pepper-like, onion-like, tobacco-like, and cooked onion omelet-like aroma and taste nuances with a lachrymatory effect in foodstuffs as set forth supra.

The furyl and phenyl mercaptals of our invention defined according to the generic structure:

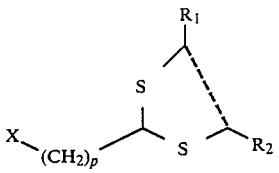

wherein the dashed line represents a carbon-carbon single bond or no bond; wherein $R_1$ and $R_2$ are the same or different and each represents hydrogen, methyl or ethyl; wherein p is 0 or 1; and wherein X represents a phenyl moiety having the structure:

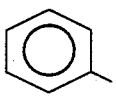

or a furyl moiety having the structure:

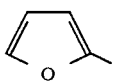

may be produced by means of reacting an alpha,beta dithiol defined according to the generic structure:

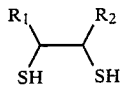

wherein $R_1$ and $R_2$ are the same or different and each represents hydrogen, methyl or ethyl or a mercaptan defined according to the structure:

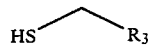

wherein $R_3$ represents one of $R_1$ or $R_2$ as defined supra with an aldehyde defined according to the structure:

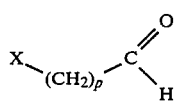

wherein X is one of the moieties phenyl having the structure:

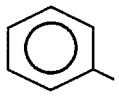

or furyl having the structure:

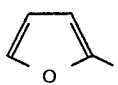

and p represents 0 or 1 in the presence of a protonic acid catalyst such as para-toluenesulfonic acid, xylene sulfonic acid, methane sulfonic acid, phosphoric acid and concentrated sulfuric acid. The reaction takes place in the presence of a solvent having a boiling point such that the reaction can proceed in a reasonable period of time, e.g. 1–12 hours, at atmospheric pressure or pressures somewhat greater than atmospheric pressure (up to about 10 atmospheres). The reaction temperature may vary from between about 70° C. up to about 140° C. Reaction temperatures greater than 140° C. give rise to unnecessary breakdown of reaction product. Reaction temperatures lower than 70° C. give rise to too long a period of time of reaction. The solvents utilized must be inert to the reaction product as well as inert to the reactants. The solvent utilized must also have a boiling point of between 70° C. and 140° C. since the reaction is to take place under reflux conditions. The reaction solvent must also be capable of being completely removed from the product on distillation in view of the fact that the reaction products are used as food flavors for internal consumption. Accordingly, suitable solvents are, for example, cyclohexane, cyclopentane, cyclooctane, 1-methylcyclohexane, 1,2-dimethylcyclohexane, 1,2,4-trimethylcyclohexane, 2-ethyltetrahydrofuran, 2,5-dimethyltetrahydrofuran and the like.

The mole ratio of aldehyde defined according to the structure:

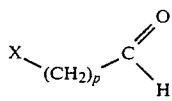

to dithiol defined according to the structure:

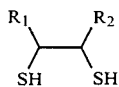

is preferably about 1:1 and the mole ratio of aldehyde having the structure:

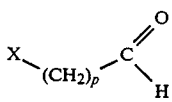

to mercaptan having the structure:

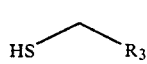

is about 1:2 since 2 moles of mercaptan having the structure:

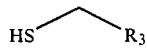

are desired to be reacted with 1 mole of aldehyde having the structure:

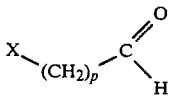

and 1 mole of dithiol having the structure:

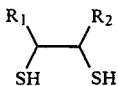

are desired to be reacted with 1 mole of aldehyde defined according to the structure:

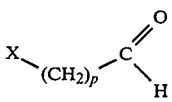

in order to make one of the compounds defined under the genus:

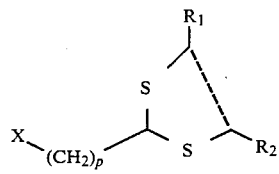

wherein the dashed line represents a carbon-carbon single bond or no bond; wherein $R_1$ and $R_2$ are the same or different and each represents hydrogen, methyl or ethyl; wherein p is 0 or 1; and wherein X represents a phenyl moiety having the structure:

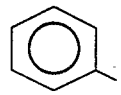

or a furyl moiety having the structure:

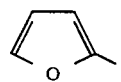

Accordingly, the reaction of our invention, generically is set forth as follows:

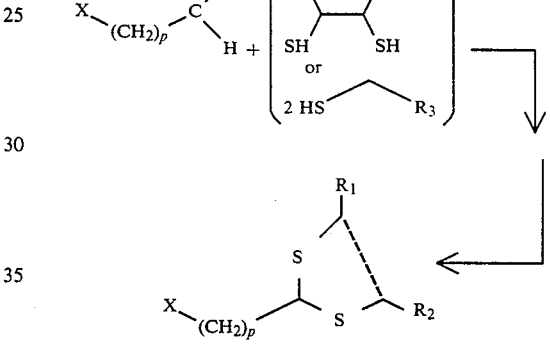

wherein the dashed line represents a carbon-carbon single bond or no bond; wherein $R_1$ and $R_2$ are the same or different and each represents hydrogen, methyl or ethyl; wherein p is 0 or 1; and wherein X represents a phenyl moiety having the structure:

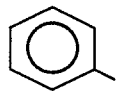

or a furyl moiety having the structure:

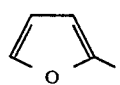

At the end of the reaction as stated supra, the reaction product is extracted from the reaction mass or the reaction mass is washed, for example, with saturated sodium chloride. The reaction product is then distilled, preferably by means of vacuum distillation using a fractionation column.

Examples of the products of our invention and their organoleptic properties are as follows:

TABLE I

| Structure of Compound | Organoleptic Properties |
|---|---|
| (phenyl-CH(S-)-CH(S-iPr)) | A roasted and green vegetable aroma and taste with a hydrolyzed vegetable protein-like aftertaste at 1 ppm causing it to be useful in roasted nut, roasted meat and beef broth flavors. |
| (phenyl-CH(S-Et)-CH2-S-nPr) | A brothy, savory and peppery aroma and taste at 5 ppm causing it to be useful in black pepper flavors. |
| (phenyl-CH(S-)(S-)- ...) | An eggy, green, herbaceous, floral and fine herbs omelet-like aroma and taste at 5 ppm causing it to be useful in fine herbs omelet flavored foodstuffs. |
| (phenyl-CH2-CH(S-)(S-iPr)) | An eggy, green and fine herbs omelet-like aroma and taste at 1 ppm causing it to be useful in fine herbs omelet flavored foodstuffs. |
| (phenyl-CH(S-)(S-iPr)) | An eggy, green, fine herbs omelet-like aroma and taste at 1 ppm causing it to be useful in fine herbs omelet flavored foodstuffs. |
| (phenyl-CH(S-)-CH(S-iPr)) | A green and black pepper-like aroma and taste profile at 1 ppm causing it to be useful in black pepper flavored foodstuffs. |
| (furyl-CH(S-)(S-)) | A green, raw onion-like, green vegetable aroma and taste with a lachrymatory effect at 1 ppm causing it to be useful in onion flavors requiring a raw onion taste and in rare roast beef and hamburger meat flavored foodstuffs. |
| (furyl-CH(S-)(S-)) | An eggy, green, tobacco-like and cooked onion omelet-like aroma and taste profile at 1 ppm causing it to be useful in cooked onion omelet flavored foodstuffs. |
| (furyl-CH(S-)(S-)) | An eggy, green, fine herbs omelet-like aroma and taste profile at 1 ppm causing the compound to be useful in fine herbs omelet flavored foodstuffs. |

When one of the furyl and phenyl mercaptals of our invention is used as a food flavor adjuvant, the nature of the co-ingredients included with one of the furyl and phenyl mercaptals in formulating the product composition will also serve to alter, modify, augment or enhance the organoleptic characteristics of the ultimate foodstuff treated therewith.

As used herein in regard to flavors, the terms "alter", "modify" and "augment" in their various forms mean "supplying or imparting flavor character or note to otherwise bland, relatively tasteless substances or augmenting the existing flavor characteristic where a natural flavor is deficient in some regard or supplementing the existing flavor impression to modify its quality, character or taste".

The term "enhance" is used herein to mean the intensification of a flavor or aroma characteristic or note without the modification of the quality thereof. Thus, "enhancement" of a flavor or aroma means that the enhancement agent does not add any additional flavor note.

As used herein, the term "foodstuff" includes both solid and liquid ingestible materials which usually do, but need not, have nutritional value. Thus, foodstuffs include soups, convenience foods, beverages, dairy products, candies, vegetables, cereals, soft drinks, snacks and the like.

Substances suitable for use herein as co-ingredients or flavoring adjuvants are well known in the art for such use, being extensively described in the relevant literature. It is a requirement that any such material be "ingestibly" acceptable and thus non-toxic and otherwise non-deleterious particularly from an organoleptic standpoint whereby the ultimate flavor and/or aroma of the consumable material used is not caused to have unacceptable aroma and taste nuances. Such materials may in general be characterized as flavoring adjuvants or vehicles comprising broadly stabilizers, thickeners, surface active agents, conditioners, other flavorants and flavor intensifiers.

Stabilizer compound include preservatives, e.g. sodium chloride; antioxidants, e.g. calcium and sodium ascorbate, ascorbic acid, butylated hydroxy-anisole (mixture of 2- and 3-tertiary-butyl-4-hydroxy-anisole), butylated hydroxy toluene (2,6-di-tertiary-butyl-4-methyl phenol), propyl gallate and the like and sequestrants, e.g. citric acid.

Thickener compounds include carriers, binders, protective colloids, suspending agents, emulsifiers and the like, e.g. agar agar, carrageenan; cellulose and cellulose derivatives such as carboxymethyl cellulose and methyl cellulose; natural and synthetic gums such as gum arabic, gum tragacanth; gelatin, proteinaceous materials; lipids; carbohydrates; starches, pectins and emulsifiers, e.g. mono- and diglycerides of fatty acids, skim mild powder, hexoses, pentoses, disaccharides, e.g. sucrose, corn syrup and the like.

Surface active agents include emulsifying agents, e.g. fatty acids such as capric acid, caprylic acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g. benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g. sodium acetate, ammonium bicarbonate, ammonium phosphate, citric acid, lactic acid, vinegar and the like; colorants, e.g. carminic acid, cochineal, tumeric and curcuma and the like; firming agents such as aluminum sodium sulfate, calcium chloride and calcium gluconate; texturizers, anti-caking agents, e.g. aluminum calcium sulfate and tribasic calcium phosphate, enzymes; yeast foods, e.g. calcium lactate and calcium sulfate; nutrient supplements, e.g. iron salts such as ferric phosphate, ferrous gluconate and the like, riboflavin, vitamins, zinc sources such as zinc chloride, zinc sulfate and the like.

Other flavorants and flavor intensifiers include organic acids, e.g. acetic acid, formic acid, 2-hexenoic acid, benzoic acid, n-butyric acid, caproic acid, caprylic acid, cinnamic acid, isobutyric acid, isovaleric acid, alpha-methyl-butyric acid, propionic acid, valeric acid, 2-methyl-2-pentenoic acid, and 2-methyl-3-pentenoic acid; ketones and aldehydes, e.g. acetaldehyde, acetophenone, acetone, acetyl methyl carbinol, acrolein, n-butanal, crotonal, diacetyl, 2-methyl butanal, beta,-beta-dimethylacrolein, methyl-n-amyl ketone, n-hexenal, 2-hexenal, isopentanal, hydrocinnamic aldehyde, cis-3-hexenal, 2-heptanal, nonyl aldehyde, 4-(p-hydroxyphenyl)-2-butanone, alpha-ionone, beta-ionone, methyl-3-butanone, benzaldehyde, damascone, damascenone, acetophenone, 2-heptanone, o-hydroxyacetophenone, 2-methyl-2-hepten-6-one, 2-octanone, 2-undecanone, 3-phenyl-4-pentenal, 2-phenyl-2-hexenal, 2-phenyl-2-pentenal, furfural, 5-methyl furfural, cinnamaldehyde, beta-cyclohomocitral, 2-pentanone, 2-pentenal and propanal; alcohols such as 1-butanol, benzyl alcohol, 1-borneol, trans-2-buten-1-ol, ethanol, geraniol, 1-hexanal, 2-heptanol, trans-2-hexenol-1, cis-3-hexen-1-ol, 3-methyl-3-buten-1-ol, 1-pentanol, 1-penten-3-ol, p-hydroxyphenyl-2-ethanol, isoamyl alcohol, isofenchyl alcohol, phenyl-2-ethanol, alpha-terpineol, cis-terpineol hydrate, eugenol, linalool, 2-heptanol, acetoin; esters such as butyl acetate, ethyl acetate, ethyl acetoacetate, ethyl benzoate, ethyl butyrate, ethyl caprate, ethyl caproate, ethyl caprylate, ethyl cinnamate, ethyl crotonate, ethyl formate, ethyl isobutyrate, ethyl isovalerate, ethyl laurate, ethyl myristate, ethyl alpha-methylbutyrate, ethyl propionate, ethyl salicylate, trans-2-hexenyl acetate, hexyl acetate, 2-hexenyl butyrate, hexyl butyrate, isoamyl acetate, isopropyl butyrate, methyl acetate, methyl butyrate, methyl caproate, methyl isobutyrate, alpha-methylphenylglycidate, ethyl succinate, isobutyl cinnamate, cinnamyl formate, methyl cinnamate and terpenyl acetate; hydrocarbons such as dimethyl naphthalene, dodecane, methyl diphenyl, methyl naphthalene, myrcene, naphthalene, octadecane, tetradecane, tetramethyl naphthalene, tridecane, trimethyl naphthalene, undecane, caryophyllene, 1-phellandrene, p-cymeme, 1-alpha-pinene, beta-pinene, dihydrocarveol; pyrazines such as 2,3-dimethyl-pyrazine, 2,5-dimethylpyrazine, 2,6-dimethylpyrazine, 3-ethyl-2,5-dimethylpyrazine, 2-ethyl-3,5,6-trimethyl-pyrazine, 3-isoamyl-2,5-dimethylpyrazine, 5-isoamyl-2,3-dimethylpyrazine, 2-isoamyl-3,5,6-trimethylpyrazine, isopropyl dimethyl-pyrazine, methyl ethylpyrazine, tetramethylpyrazine, trimethyl-pyrazine; essential oils such as jasmine absolute, cassia oil, cinnamon bark oil, black pepper oleoresin, oil of black pepper, rose absolute, orris absolute, oil of cubeb, oil of coriander, oil of pimento leaf, oil of patchouli, oil of nutmeg, lemon essential oil, safran oil, Bulgarian rose oil, capsicum, yara yara and vanilla; lactones such as gamma-nonalactone; sulfides, e.g. allyl propenyl disulfide, dipropyl disulfide, dipropyl trisulfide, diallyl disulfide, diallyl trisulfide, 2-methyl-3-furyl methyl sulfide and bis(2-methyl-3-furyl) disulfide and other materials such as maltol, acetoin, acetals (e.g. 1,1-diethoxyethane, 1,1-dimethoxyethane, dimethoxymethane, 1-acetoxy-1-ethoxyethane and 1-acetoxy-1-methoxyethane), piperine, chavicine, piperidine, 2,5-dimethyl-3-acetyl furan, 2,5-dimethyl-3-acetyl thiophene and reaction products such as the reaction products described in U.S. Pat. Nos. 3,394,015, 3,394,016, 3,394,017, 3,682,692, 3,782,973 and 4,045,587, the disclosures of which are incorporated by reference herein.

The specific flavor adjuvants selected for use may be either solid or liquid depending upon the desired physical form of the ultimate produce, i.e. foodstuff, whether simulated or natural, and should, in any event, (i) be organoleptically compatible with one of the furyl and phenyl mercaptals of our invention by not covering or spoiling the organoleptic properties (aroma or taste) thereof; (ii) be nonreactive with the furyl and phenyl mercaptals of our invention and (iii) be capable of providing an environment in which one of the furyl and phenyl mercaptals of our invention can be dispersed or admixed to provide a homogeneous medium. In addition, selection of one or more flavoring adjuvants, as well as the quantities thereof will depend upon the precise organoleptic character desired in the finished product. Thus, in the case of flavoring compositions, ingredient selection will vary in accordance with the foodstuff to which the flavor and/or aroma are to be imparted, modified, altered or enhanced. In contradistinction, in the preparation of solid products, e.g. simulated foodstuffs, ingredients capable of providing normally solid compositions should be selected such as various cellulose derivatives.

As will be appreciated by those skilled in the art, the amount of one of the furyl and phenyl mercaptals employed in a particular instance can vary over a relatively wide range, depending upon the desired organoleptic effects to be achieved. Thus, correspondingly greater amounts would be necessary in those instances wherein the ultimate food composition to be flavored is relatively bland to the taste, whereas relatively minor quantities may suffice for purposes of enhancing the composition merely deficient in natural flavor or aroma. The primary requirement is that the amount selected to be effective, i.e. sufficient to alter, modify or enhance the organoleptic characteristics of the parent composition, whether foodstuff per se, chewing gum per se, medicinal product per se, toothpaste per se, or flavoring composition.

The use of insufficient quantities of one of the furyl and phenyl mercaptals will, of course, substantially vitiate any possibility of obtaining the desired results while excess quantities prove needlessly costly and, in extreme case, may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, chewing gum compositions, medicinal product compositions and toothpaste compositions, it is found that quantities of one of the furyl and phenyl mercaptals ranging from a small but effective amount, e.g. 0.05 parts per million up to about 100 parts per million based on total composition, are suitable. Concentrations in excess of the maximum quantity stated are not normally recommended, since they fail to provide commensurate enhancement of organoleptic properties. In those instances wherein one of the furyl and phenyl mercaptals of our invention is added to the foodstuff as an integral component of a flavoring composition, it is, of course, essential that the total quantity of flavoring composition employed be sufficient to yield an effective furyl and phenyl mercaptal concentration in the foodstuff product.

Food flavoring compositions prepared in accordance with the present invention preferably contain one of the furyl and phenyl mercaptals in concentrations ranging from about 0.1% up to about 15% by weight based on the total weight of the said flavoring composition.

The composition described herein can be prepared according to conventional techniques well known as typified by meat pie crust batters and proteinaceous drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing one of the furyl and phenyl mercaptals with, for example, gum arabic, gum tragacanth, carrageenan and the like, and thereafter spray-drying the resultant mixture whereby to obtain the particulate solid product. Pre-prepared flavor mixes in powder form, e.g. onion-flavored powder mix, are obtained by mixing the dried solid components, e.g. starch, sugar and the like, and one of the furyl and phenyl mercaptals of our invention in a dry blender until the requisite degree of uniformity is achieved.

It is presently preferred to combine with one of the furyl and phenyl mercaptals of our invention, the following adjuvants:
Oil of cubeb;
Phellandrene;
Oil of coriander;
Oil of pimento leaf;
Oil of patchouli;
Alpha pinene;
Beta-pinene;
Beta-caryophyllene;
Dihydrocarveol;
Piperonal;
Piperine;
Oil of black pepper;
Black pepper oleoresin;
Capsicum;
Oil of nutmeg;
Bis(2-methyl-3-furyl)disulfide;
Reaction products which produce meat flavors such as the reaction product of hydrogen sulfide and 2- or 5-monoalkyl and 2,5-dialkyl-4-hydroxy-2,3-dihydrofuran-3-ones;
Diallyl trisulfide;
Propyl propenyl trisulfide;
Propyl propenyl disulfide;
Propyl allyl disulfide;
Propyl allyl trisulfide;
1-propenyl allyl trisulfide;
Di(1-propenyl)disulfide;
Di(1-propenyl)trisulfide;
Thioethanal-S-oxide;
Propyl propene thiosulfonate;
Thiobutanal-S-oxide;
Thiohexanal-S-oxide;
Propyl propane thiosulfonate;
Propyl propenyl thiosulfonate;
4-Terpinenol propionate;
The reaction product of hydrolyzed vegetable protein, cysteine and thiamine as described in U.S. Pat. No. 3,394,015, in specification of which is incorporated by reference herein.

The following examples serve to illustrate the utility and process for preparing the furyl and phenyl mercaptals of our invention. It will be understood that these examples are illustrative and the invention is to be considered restricted thereto only as indicated in the appended claims.

All parts and percentages given herein are by weight unless otherwise specified.

EXAMPLE I

PREPARATION OF 4-METHYL-2-PHENYL-1,3-DITHIOLANE

Reaction:

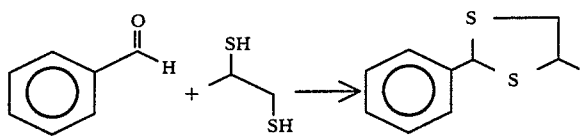

Into a 100 ml flask equipped with reflux condenser and magnetic stirring bar with hot plate and magnetic stirring apparatus is placed 0.5 grams of para-toluenesulfonic acid, 5.0 ml cyclohexane and 5.4 grams (0.05 moles) of 1,2-propanedithiol. With stirring over a period of 30 minutes, 5.3 grams (0.05 moles) of benzaldehyde is added to the reaction mass. The reaction mass with stirring is then heated to reflux and is refluxed for a period of 8 hours during which time water of reaction is removed from the reaction mass. The reaction mass is then cooled and transferred to a separatory funnel. The resulting reaction mass is washed with one 50 ml portion of saturated sodium chloride solution, dried over anhydrous sodium sulfate and filtered. The resulting filtrate is distilled on a Microvigreux column yielding the following fractions:

| Fraction Number | Vapor Temp. (°C.) | Liquid Temp (°C.) | Vacuum mm/Hg. |
|---|---|---|---|
| 1 | 115 | 128 | 2 |
| 2 | 118 | 134 | 2 |
| 3 | 100 | 150 | 2 |

FIG. 1 is the GLC profile for fraction 3 of the foregoing distillation containing the compound having the structure:

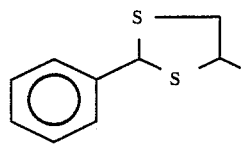

(conditions: 10'×0.125" SE-30 column programmed at 100°-220° C. at 8° C. per minute).

FIG. 2 is the NMR spectrum for the above fraction 3 of the distillation product containing the compound having the structure:

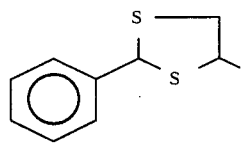

(conditions: Field Strength: 100 MHz; Solvent: CFCl₃).

EXAMPLE II

PREPARATION OF 2-BENZYL-4,5-DIMETHYL-1,3-DITHIOLANE

Reaction:

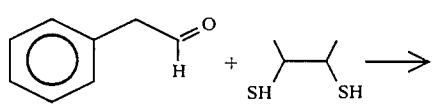

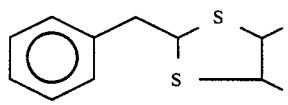

Into a 100 ml flask equipped with reflux condenser and magnetic stirring bar and hot plate equipped with magnetic stirring apparatus is placed 0.2 grams of para-toluenesulfonic acid, 5 ml cyclohexane and 6.1 grams (0.05 moles) of 2,3-butanedithiol. With stirring, over a period of 30 minutes, 6.0 grams (0.05 moles) of phenylacetaldehyde is added to the reaction mass. The reaction mass is then heated to reflux and refluxed for a period of 10 hours during which time water of formation is removed. After the 10 hour period, the reaction mass is cooled and transferred to a separatory funnel. The reaction mass is washed with one 50 ml portion of saturated sodium chloride, dried over anhydrous sodium sulfate and filtered. The resulting filtrate is then distilled on a Microvigreux column yielding the following four fractions:

| Fraction Number | Vapor Temp. (°C.) | Liquid Temp. (°C.) | Vacuum mm/Hg |
|---|---|---|---|
| 1 | 114 | 130 | 2 |
| 2 | 128 | 140 | 2 |
| 3 | 128 | 144 | 2 |
| 4 | 120 | 150 | 2 |

FIG. 3 is the GLC profile for the crude reaction product containing the compound having the structure:

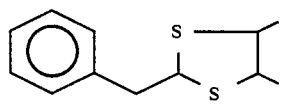

FIG. 4 is the GLC profile for fraction 4 of the foregoing distillation containing the compound having the structure:

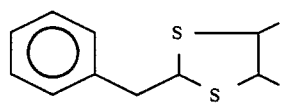

(conditions: 10'×0.125" SE-30 column programmed at 100°–220° C. at 8° C. per minute).

FIG. 5 is the NMR spectrum for fraction 3 of the foregoing distillation containing the compound having the structure:

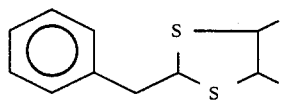

(conditions: Field Strength: 100 MHz; Solvent: CFCl₃).

EXAMPLE III

PREPARATION OF BENZALDEHYDE DIPROPYL MERCAPTAL

Reaction:

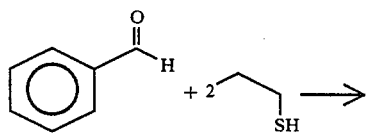

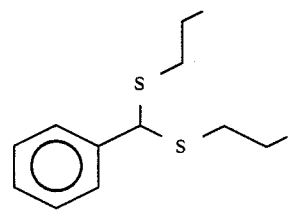

Into a 100 cc reaction flask equipped with reflux condenser, magnetic stirring bar, and hot plate equipped with magnetic stirring apparatus is placed 10 ml cyclohexane, 0.5 grams of para-toluenesulfonic acid and 15.2 grams (0.2 moles) of n-propyl mercaptan. Over a period of 25 minutes with stirring is added 10.6 grams (0.1 moles) of benzaldehyde. The reaction mass is heated to reflux with stirring and refluxed for a period of 7 hours. During the refluxing, water of reaction is removed. At the end of the 7 hour period, the reaction mass is cooled to room temperature and transferred to a separatory funnel. The reaction mass is then washed with one 50 ml portion of a saturated aqueous sodium chloride solution and then dried over anhydrous sodium sulfate and filtered. The resulting filtrate is distilled on a Microvigreux column yielding the following five fractions:

| Fraction Number | Vapor Temp. (°C.) | Liquid Temp. (°C.) | Vacuum mm/Hg. |
|---|---|---|---|
| 1 | 151 | 162 | 2 |
| 2 | 153 | 162 | 2 |
| 3 | 150 | 160 | 2 |
| 4 | 150 | 160 | 2 |
| 5 | 120 | 170 | 2 |

FIG. 6 is the GLC profile for fraction 4 of the foregoing distillation containing the compound having the structure:

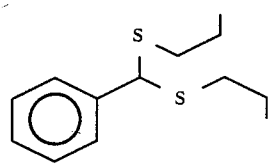

(conditions: 10'×0.125" SE-30 column programmed at 100°–220° C. at 8° C. per minute).

FIG. 7 is the NMR spectrum for fraction 4 of the foregoing distillation containing the compound having the structure:

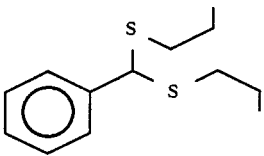

(conditions: Field Strength: 100 MHz; Solvent: CFCl₃).

EXAMPLE IV

PREPARATION OF 2-BENZYL-4-METHYL-1,3-DITHIOLANE

Reaction:

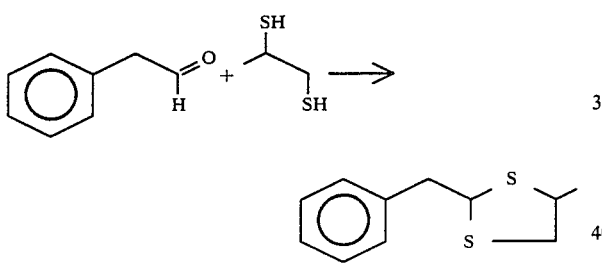

Into a 100 cc reaction flask equipped with reflux condenser, magnetic stirring bar and thermometer and hot plate equipped with magnetic stirring apparatus is placed 5 ml cyclohexane, 0.2 grams of para-toluenesulfonic acid and 5.4 grams (0.05 moles) of 1,2-propanedithiol. With stirring, over a period of 30 minutes, 6 grams (0.05 moles) of phenylacetaldehyde is added to the reaction mass. The reaction mass is then heated to reflux and refluxed for a period of 8 hours. During the refluxing period, water of reaction is removed. At the end of the refluxing period, the reaction mass is cooled to room temperature and transferred to a separatory funnel. The reaction mass is then washed with one 50 ml portion of saturated aqueous sodium chloride solution, dried over anhydrous sodium sulfate and filtered. The resulting filtrate is distilled on a Microvigreux column yielding the following three fractions:

| Fraction Number | Vapor Temp. (°C.) | Liquid Temp. (°C.) | Vacuum mm/Hg. |
|---|---|---|---|
| 1 | 120 | 138 | 2 |
| 2 | 123 | 138 | 2 |
| 3 | 121 | 145 | 2 |

FIG. 8 is the GLC profile for fraction 3 of the foregoing distillation containing the compound having the structure:

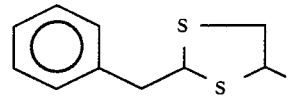

(conditions: 10'×0.125" SE-30 column programmed at 100°–220° C. at 8° C. per minute).

FIG. 9 is the NMR spectrum for fraction 3 of the foregoing distillation containing the compound having the structure:

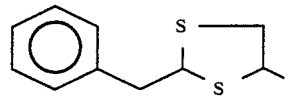

(conditions: Field Strength: 100 MHz; Solvent: CFCl₃).

EXAMPLE V

PREPARATION OF PHENYL ACETALDEHYDE DIPROPYL MERCAPTAL

Reaction:

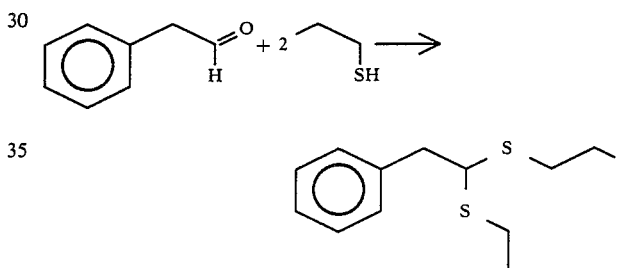

Into a 100 ml reaction flask equipped with thermometer, reflux condenser and magnetic stirring bar and hot plate equipped with magnetic stirring apparatus is placed 0.2 grams of para-toluenesulfonic acid, 5 ml cyclohexane and 7.6 grams (0.1 mole) of n-propyl mercaptan. With stirring over a period of 25 minutes, 6 grams (0.05 moles) of phenyl acetaldehyde is added to the reaction mass. The reaction mass is then heated to reflux and refluxed for a period of 8.5 hours. During the refluxing period, water of reaction is removed. At the end of the refluxing period, the reaction mass is cooled to room temperature and transferred to a separatory funnel. The reaction mass is washed with one 50 ml portion of saturated aqueous sodium chloride solution, and then dried over anhydrous sodium sulfate and filtered. The filtrate is distilled on a Microvigreux column yielding the following five fractions:

| Fraction Number | Vapor Temp. (°C.) | Liquid Temp. (°C.) | Vacuum mm/Hg. |
|---|---|---|---|
| 1 | 100 | 140 | 2 |
| 2 | 135 | 155 | 2 |
| 3 | 137 | 156 | 2 |
| 4 | 138 | 155 | 2 |
| 5 | 130 | 160 | 2 |

FIG. 10 is the GLC profile for the crude reaction product containing the compound having the structure:

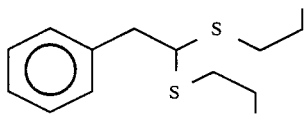

FIG. 11 is the GLC profile for fraction 4 of the foregoing distillation containing the compound having the structure:

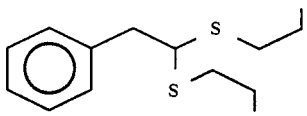

(conditions: 10'×0.125" SE-30 column programmed at 100°-220° C. at 8° C. per minute).

FIG. 12 is the NMR spectrum for fraction 4 of the foregoing distillation containing the compound having the structure:

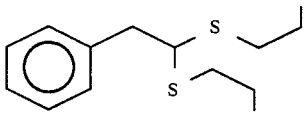

(conditions: Field Strength: 100 MHz; Solvent: CFCl₃).

EXAMPLE VI

PREPARATION OF 4,5-DIMETHYL-2-PHENYL-1,3-DITHIOLANE

Reaction:

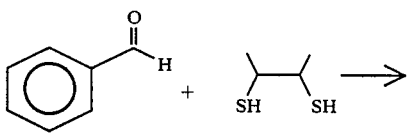

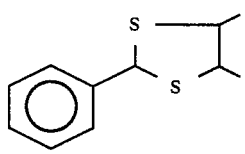

Into a 100 ml reaction flask equipped with thermometer, reflux condenser and magnetic stirring bar and hot plate with magnetic stirring apparatus is placed 0.5 grams of para-toluenesulfonic acid, 5.0 ml cyclohexane and 6.1 grams (0.05 moles) of 2,3-butanedithiol. Over a period of 25 minutes, 5.3 grams (0.05 moles) of benzaldehyde is added to the reaction mass with stirring. The reaction mass is then heated to reflux with stirring and refluxed for a period of 9.5 hours while taking off water of reaction. At the end of the refluxing period, the reaction mass is cooled to room temperature and transferred to a separatory funnel. The reaction mass is then washed with one 50 ml portion of saturated aqueous sodium chloride solution, dried over anhydrous sodium sulfate and filtered. The resulting filtrate is distilled on a Microvigreux column yielding the following three fractions:

| Fraction Number | Vapor Temp. (°C.) | Liquid Temp. (°C.) | Vacuum mm/Hg. |
|---|---|---|---|
| 1 | 115 | 140 | 2 |
| 2 | 120 | 143 | 2 |
| 3 | 110 | 150 | 2 |

FIG. 13 is the GLC profile for fraction 2 of the foregoing distillation containing the compound having the structure:

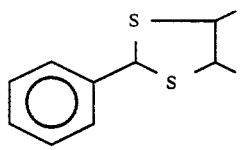

FIG. 14 is the NMR spectrum for fraction 2 of the foregoing distillation containing the compound having the structure:

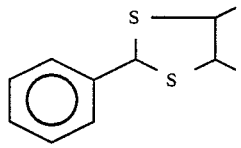

(conditions: Field Strength: 100 MHz; Solvent: CFCl₃).

EXAMPLE VII

PREPARATION OF 2-FURALDEHYDE DIPROPYL MERCAPTAL

Reaction:

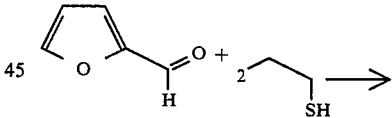

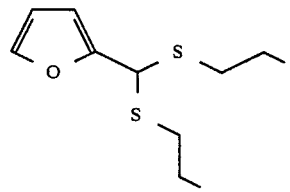

Into a 100 ml reaction flask equipped with reflux condenser, thermometer and magnetic stirring bar with hot plate and magnetic stirring apparatus is placed 0.5 grams of para-toluenesulfonic acid, 5 ml cyclohexane and 15.2 grams (0.2 moles) of n-propyl mercaptan. Over a period of 25 minutes, 9.6 grams (0.1 mole) of 2-furaldehyde is added with stirring. The reaction mixture is then heated to reflux and refluxed for a period of 10 hours while removing water of reaction. The the end of the 10 hour reflux period, the reaction mass is cooled to room temperature and transferred to a separatory funnel. The reaction mass is washed with one 50 ml portion of saturated aqueous sodium chloride solution and dried over anhydrous sodium sulfate and filtered. The resulting filtrate is then distilled on a Microvigreux column yielding the following fractions:

| Fraction Number | Vapor Temp. (°C.) | Liquid Temp. (°C.) | Vacuum mm/Hg. |
|---|---|---|---|
| 1 | 112 | 123 | 2 |
| 2 | 113 | 125 | 2 |
| 3 | 105 | 130 | 2 |

FIG. 15 is the GLC profile for fraction 2 of the foregoion distillation containing the compound having the structure:

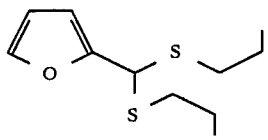

(conditions: 10'×0.125" SE-30 column programmed at 100°-220° C. at 8° C. per minute).

FIG. 16 is the NMR spectrum for fraction 2 of the foregoing distillation containing the compound having the structure:

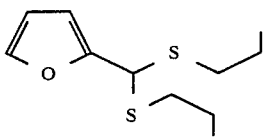

(conditions: Field Strength: 100 MHz; Solvent: CFCl₃).

EXAMPLE VIII

PREPARATION OF 2-(2-FURYL)-4,5-DIMETHYL-1,3-DITHIOLANE

Reaction:

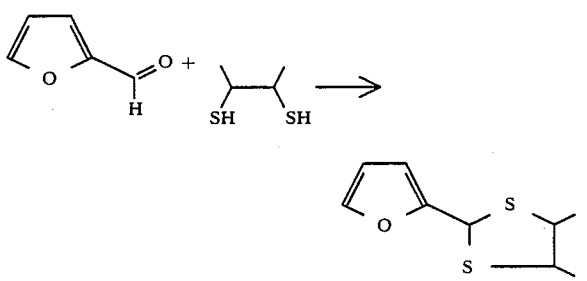

Into a 100 ml reaction flask equipped with magnetic stirring bar, thermometer and reflux condenser and hot plate with magnetic stirring apparatus is placed 0.5 grams para-toluenesulfonic acid, 5 ml cyclohexane and 6.1 grams (0.05 moles) of 2,3-butanedithiol. Over a period of 35 minutes, 4.8 grams (0.05 moles) of 2-furaldehyde is added to the reaction mass with stirring. The reaction mass is then heated to reflux and refluxed for a period of 7.5 hours with stirring while removing water of reaction. After the refluxing period, the reaction mass is cooled to room temperature and transferred to a separatory funnel. The reaction mass is then washed with one 50 ml portion of saturated sodium chloride solution and dried over anhydrous sodium sulfate and filtered. The resulting filtrate is distilled using a Microvigreux column yielding the following fractions:

| Fraction Number | Vapor Temp. (°C.) | Liquid Temp. (°C.) | Vacuum mm/Hg. |
|---|---|---|---|
| 1 | 100 | 105 | 2 |
| 2 | 101 | 107 | 2 |
| 3 | 95 | 120 | 2 |

FIG. 17 is the GLC profile for fraction 3 of the foregoing distillation containing the compound having the structure:

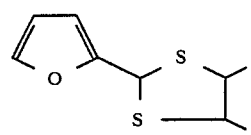

(conditions: 10'×0.125" SE-30 column programmed at 100°-220° C. at 8° C. per minute).

FIG. 18 is the NMR spectrum for fraction 3 of the foregoing distillation containing the compound having the structure:

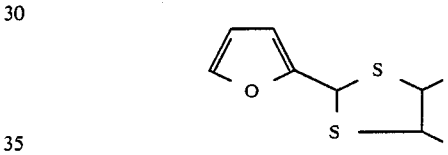

(conditions: Field Strength: 100 MHz; Solvent: CFCl₃).

EXAMPLE IX

PREPARATION OF 2-(2-FURYL)-4-METHYL-1,3-DITHIOLANE

Reaction:

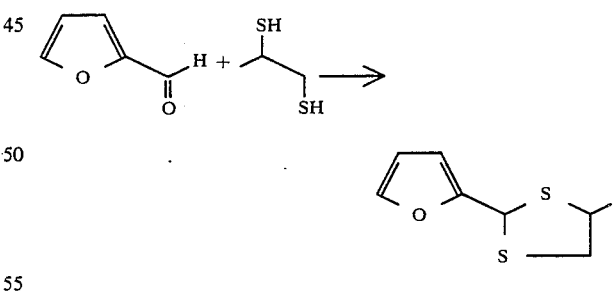

Into a 100 ml reaction flask equipped with reflux condenser, thermometer and magnetic stirring bar and hot plate with magnetic stirring apparatus is placed 0.5 grams paratoluenesulfonic acid, 5 ml cyclohexane and 5.4 grams (0.05 moles) of 1,2-propanedithiol. Over a period of 25 minutes with stirring is added 4.8 grams (0.05 moles) of 2-furaldehyde. The reaction mass is then heated to reflux and refluxed for a period of 8 hours while removing water of reaction. At the end of the refluxing period, the reaction mass is cooled to room temperature and transferred to a separatory funnel. The reaction mass is washed with one 50 ml portion of aqueous saturated sodium chloride, and dried over anhydrous sodium sulfate. The reaction mass is then filtered and the filtrate is distilled on a Microvigreux column yielding the following three fractions:

| Fraction Number | Vapor Temp. (°C.) | Liquid Temp. (°C.) | Vacuum mm/Hg. |
|---|---|---|---|
| 1 | 96 | 105 | 2 |
| 2 | 100 | 110 | 2 |
| 3 | 90 | 120 | 2 |

FIG. 19 is the GLC profile for fraction 2 of the foregoing distillation containing the compound having the structure:

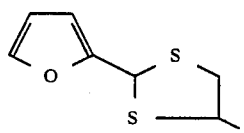

(conditions: 10'×0.125" SE-30 column programmed at 100°-220° C. at 8° C. per minute).

FIG. 20 is the NMR spectrum for fraction 2 of the foregoing distillation containing the compound having the structure:

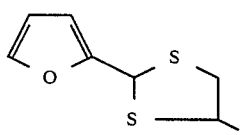

(conditions: Field Strength: 100 MHz; Solvent: CFCl$_3$).

EXAMPLE X

The compound having the structure:

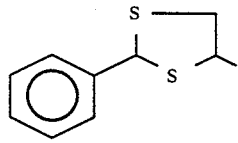

produced according to Example I is added at the level of 1 ppm (in a propylene glycol solution containing 0.1% of the compound) at the rate of 0.9 cc to 7.3 grams of a soup base consisting of:

| Ingredient | Quantity (Parts/100 total) |
|---|---|
| Fine ground sodium chloride | 35.62 |
| Hydroxyzed vegetable protein (4 BE:Nestle's) | 27.40 |
| Monosodium glutamate | 17.81 |
| Sucrose | 10.96 |
| Beef fat | 5.48 |
| Sethness caramel color (powder B & C) | 2.73 |

The resulting mixture is added to 12 oz. of boiling water to create a soup having an excellent roasted hydrolyzed vegetable protein-like aroma and taste with intense green vegetable nuances and an overall good roast beef character.

EXAMPLE XI

IMITATION OIL OF BLACK PEPPER FLAVOR FORMULATION

The following mixture is prepared:

| Ingredients | Parts by Weight |
|---|---|
| Oil of cubeb | 40.0 |
| Alpha phellandrene | 35.0 |
| Oil of coriander | 9.0 |
| Oil of pimento leaf | 3.0 |
| Oil of patchouli | 0.2 |
| Alpha pinene | 1.5 |
| Beta Pinene | 3.0 |
| Beta caryophyllene | 4.0 |
| Dihydrocarveol | 1.0 |
| Piperonal | 0.8 |
| Piperine | 1.0 |
| Piperidine | 1.5 |
| | 100.0 total |

To half of this formulation, 5% by weight of the compound having the structure:

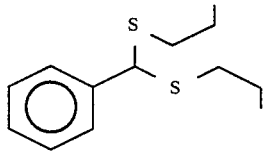

produced according to Example III is added. Nothing is added to the other half. Both formulations are diluted in food grade ethyl alcohol at levels of 10 ppm, 20 ppm, 50 ppm, 100 ppm, 150 ppm and 200 ppm. In each of the comparisons at each of the levels, the formulations containing the compound having the structure:

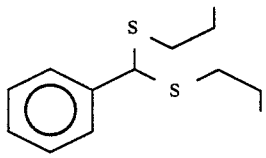

produced according to Example III had a stronger, more natural-like, black pepper aroma and flavor characteristic with excellent and pleasant brothy and savory nuances. Accordingly, the compound having the structure:

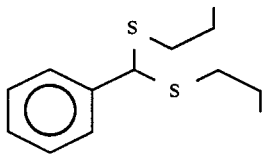

produced according to Example III is considered to advantageously augment the standard black pepper oil (imitation) making it more natural-like.

EXAMPLE XII

An omelet is produced using a bland margarine and dried prepared eggs (as utilized in an army field kitchen platter). The omelet is split up into six portions. To the first portion nothing is added. To the second portion the compound having the structure:

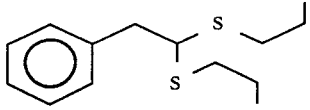

produced according to Example V is added. To the third portion the compound having the structure:

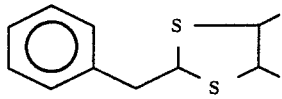

prepared according to Example II is added. To the fourth portion the compound having the structure:

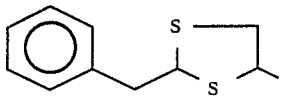

prepared according to Example IV is added. To the fifth portion the compound having the structure:

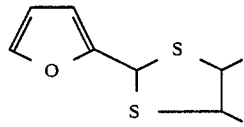

prepared according to Example VIII is added. To the sixth portion the compound having the structure:

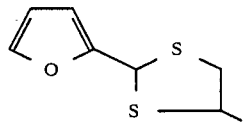

prepared according to Example IX is added. Each of the compounds is added at the level of 5 ppm to the omelet during the cooking of same with the bland margarine.

The compound having the structure:

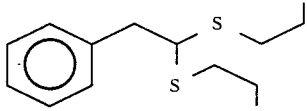

prepared according to Example V adds to this bland omelet an interesting natural egg, fine herbs omelet-like aroma and taste profile.

The compound having the structure:

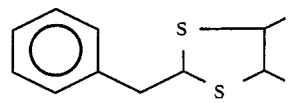

prepared according to Example II adds a natural, egg-like, fine herbs omelet-like aroma and taste profile to this otherwise bland omelet.

The compound having the structure:

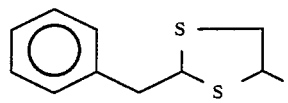

prepared according to Example IV adds a natural egg-like, fine herbs omelet-like aroma and taste profile to this otherwise bland omelet.

The compound having the structure:

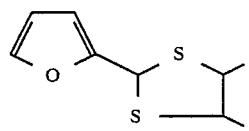

prepared according to Example VIII adds a natural egg, cooked onion omelet-like aroma and taste profile to this otherwise bland omelet.

The compound having the structure:

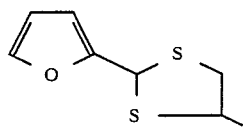

prepared according to Example IX adds a natural egg, fine herbs omelet-like aroma and taste profile to this otherwise bland omelet. At levels up to 20 ppm, the same effect is found.

A bench panel of five independent members, independent of the assignee of the instant application, unanimously prefers each of the compounds defined according to the structures:

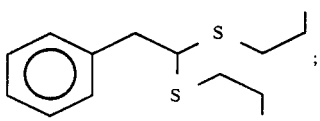

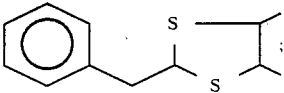

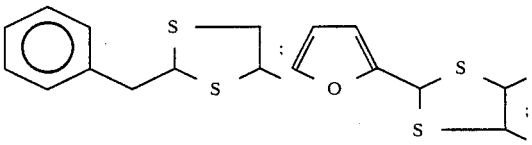

and 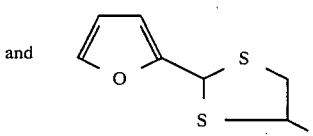

to the egg omelet not having these materials added thereto.

EXAMPLE XIII 10 ppm of the compound defined according to the structure:

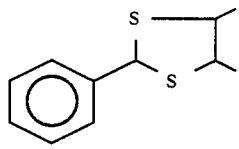

prepared according to Example VI is added to West Indian Nutmeg Oil. This nutmeg oil is then used in an amount of 10% of a standard seasoning formula. This standard seasoning formula is then added to the following materials, separately:
 liver sausage
 frankfurters
 poultry dressing.

Each of the materials to which the nutmeg oil is added has an enhanced black pepper nuance and, in addition, an added "rare" note. Although a natural black pepper aroma appears to be present, the aroma is not so overpowering as to detract from the desired specific flavors of these materials.

EXAMPLE XIV

The compound having the structure:

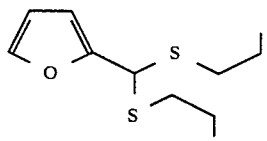

produced according to Example VII is dissolved in 95% ethanol to provide a 2% solution and is held at room temperature for 24 hours. It is then diluted with water and the water solution is added to a chicken broth to obtain a concentration of 2.5 ppm. It is found that the chicken taste is deepened and a light onion aftertaste is added. Increasing the concentration to 5 ppm adds an onion aroma and a fresh onion taste is dominating.

Repetition of the foregoing with beef broth shows a slight lachrymatory aroma and an improved general taste at a level of 4 ppm and a dominating onion note with beef broth changed to onion soup at 10 ppm.

It is judged that this flavor additive having the structure:

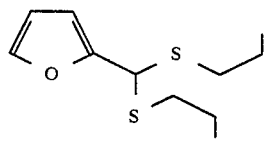

can replace flavors where fresh onion is used and it is interesting enough to be used alone to develop onion soup flavor characteristics.

What is claimed is:

1. The mercaptal having the structure:

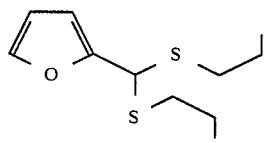

2. The mercaptal having the structure:

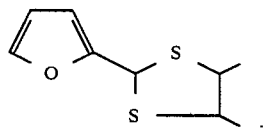

3. The mercaptal having the structure:

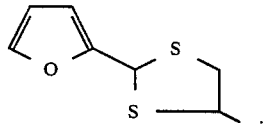

* * * * *